(12) United States Patent
Kriegstein et al.

(10) Patent No.: US 11,564,949 B2
(45) Date of Patent: *Jan. 31, 2023

(54) AMELIORATING NERVOUS SYSTEMS DISORDERS

(71) Applicant: The Regents of the University of California, Oakland, CA (US)

(72) Inventors: Arnold Kriegstein, Mill Valley, CA (US); John L. R. Rubenstein, San Francisco, CA (US); Scott C. Baraban, Novato, CA (US); Arturo Alvarez-Buylla, Woodside, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/993,914

(22) Filed: Aug. 14, 2020

(65) Prior Publication Data

US 2021/0060082 A1 Mar. 4, 2021

Related U.S. Application Data

(63) Continuation of application No. 16/144,786, filed on Sep. 27, 2018, now Pat. No. 10,780,131, which is a continuation of application No. 14/943,916, filed on Nov. 17, 2015, now Pat. No. 10,206,953, which is a continuation of application No. 13/744,201, filed on Jan. 17, 2013, now Pat. No. 9,220,729, which is a continuation of application No. 12/991,367, filed as application No. PCT/US2009/042914 on May 5, 2019, now abandoned.

(60) Provisional application No. 61/050,980, filed on May 6, 2008.

(51) Int. Cl.
  *A61K 35/30* (2015.01)
  *C12N 5/079* (2010.01)
  *A61K 9/00* (2006.01)

(52) U.S. Cl.
  CPC ............ *A61K 35/30* (2013.01); *A61K 9/0019* (2013.01); *A61K 9/0085* (2013.01); *C12N 5/0618* (2013.01); *C12N 5/0622* (2013.01); *C12N 2506/02* (2013.01); *G01N 2800/28* (2013.01); *G01N 2800/2835* (2013.01); *G01N 2800/2842* (2013.01)

(58) Field of Classification Search
  CPC .... A61K 35/30; A61K 9/0019; A61K 9/0085; C12N 5/0618; C12N 5/0622; C12N 2506/02; G01N 2800/28; G01N 2800/2835; G01N 2800/2842; A61P 25/00; A61P 25/02; A61P 25/14
  See application file for complete search history.

(56) References Cited

U.S. PATENT DOCUMENTS

| | | | |
|---|---|---|---|
| 6,087,168 A | 7/2000 | Levesque et al. |
| 6,258,353 B1 | 7/2001 | Isacson et al. |
| 6,444,205 B2 | 9/2002 | Dinsmore et al. |
| 7,955,595 B2 | 6/2011 | During et al. |
| 2002/0031497 A1 | 3/2002 | Fraser et al. |
| 2005/0191745 A1 | 9/2005 | Wahlberg et al. |
| 2008/0044901 A1 | 2/2008 | Sasai et al. |
| 2009/0311222 A1 | 12/2009 | Baraban et al. |
| 2011/0165129 A1 | 7/2011 | Krieg stein et al. |

FOREIGN PATENT DOCUMENTS

WO  WO 2007084957  7/2007

OTHER PUBLICATIONS

Castro-Lopes et al., Eur J Neurosci, 4:296-301, 1992. (Year: 1992).*
Alvarez-Dolado et al. (2006) "Cortical Inhibition Modified by Embryonic Neural Precursors Grafted into the Postnatal Brain" J Neurosci 26(28):7380-7389.
Anderson, et al., Distinct cortical migrations from the medial and lateral ganglionic eminences, Development, vol. 128, Issue 3 353-363, Copyright © 2001 by Company of Biologists.
Baraban, et al., Reduction of seizures by transplantation of cortical GABAergic interneuron precursors into Kv1.1 mutant mice, PNAS Sep. 8, 2009 vol. 106 No. 36 15472-15477.
Bejjani (2000) "Bilateral subthalamic stimulation for Parkinson's disease by using three-dimensional stereotactic magnetic resonance imaging and electrophysiological guidance" J Neurosurg 92(4):615-625.
Benninger, et al., Functional Integration of Embryonic Stem Cell-Derived Neurons in Hippocampal Slice Cultures, The Journal of Neuroscience, Aug. 6, 2003, 23(18):7075-7083.
Bjorklund & Lindvall (2000) "Cell replacement therapies for central nervous system disorders" Nat Neurosci. 3 (6):537-44.
Bosch, et al. (2004) "Induction of GABAergic phenotype in a neural stem cell line for transplantation in an excitotoxic model of Huntington's disease" Exp Neurol. 190(1):42-58.
Braz, et ai."Forebrain GABAergic neuron precursors integrate into adult spinal cord and reduce injury-induced neuropathic pain", Neuron., 2012, 74(4): 663-675.
Butt, et al. (2005) The temporal and spatial origins of cortical interneurons predict their physiological subtype Neuron 48(4):591-604.
Calcagnotio, et al., Inhibitory synaptic transmission in rodents grafted with neuronal precursors from the medial ganglionic eminence, Epilepsia 43 suppl. 7:137 (Abst 2.030), 2002.
Carpenter, et al., In Vitro Expansion of a Multipotent Population of Human Neural Progenitor Cells., Experimental Neurology, vol. 158, Issue 2, Aug. 1999, pp. 265-278.

(Continued)

*Primary Examiner* — Kimberly Ballard
*Assistant Examiner* — Stacey N MacFarlane
(74) *Attorney, Agent, or Firm* — Shweta Chandra; Bozicevic, Field & Francis LLP

(57) ABSTRACT

The present disclosure provides methods for the treatment of a mammal having a neurological condition, disease, or injury. The methods involve increasing the number of functional GABAergic interneurons at or near the site of the neurological disease, injury, or condition.

20 Claims, 13 Drawing Sheets

(56) References Cited

OTHER PUBLICATIONS

Chalmers-Redman, et al., In vitro propagation and inducible differentiation of multipotential progenitor cells from human fetal brain., Neuroscience_ Feb. 1997;76(4):1121-1128.
Chu et al. (2004) "Human neural stem cell transplantation reduces spontaneous recurrent seizures following pilocarpine-induced status epilepticus in adult rats" Brain Res 10 23(2):213-221.
Cobos, et at, Mice lacking Dlx1 show subtype-specific loss of interneurons, reduced inhibition and epilepsy, Nature Neuroscience, vol. 8, No. 8, Aug. 2005, pp. 1059-1067.
Cuevas, et al., Transient maternal hypothyroxinemia at onset of corticogenesis alters tangential migration of medial ganglionic eminence-derived neurons, European journal of neuroscience, 2005, vol. 22, No. 3, pp. 541-551.
de Lanerolle, et al., Hippocampal interneuron loss and plasticity in human temporal lobe epilepsy, Brain Res.; 495(2):387-95, 1989.
Dunnett et al. (1988) "Striatal grafts in rats with unilateral neostriatal lesions. III. Recovery from dopamine-dependent motor asymmetry and deficits in skilled paw reaching" Neuroscience, 24:813-820.
Eaton, et al., Transplants of neuronal cells bio-engineered to synthesize GABA alleviate chronic neuropathic pain. Cell Transplant 1999;8:87-101.
Eriksson, et al., Neuronal differentiation following transplantation of expanded mouse neurosphere cultures derived from different embryonic forebrain regions, Experimental neurology, 2003, vol. 184, No. 2, pp. 615-635.
Fine, et al. Modulation of experimentally induced epilepsy by intracerebral grafts of fetal GABAergic neurons, Neuropsychologia. 1990;28(6):627-34.
Finley, et al., Synapse formation and establishment of neuronal polarity by P19 embryonic carcinoma cells and embryonic stem cells., 1996, Journal of Neuroscience, vol. 16, 1056-1065.
Gernert, et al. Genetically engineered GABA-producing cells demonstrate anticonvulsant effects and long-term transgene expression when transplanted into the central piriform cortex of rats. Exp Neurol. Jul. 2002;176(1):183-92.
Gertz, et al. "Transplantation of inhibitory neuron precursors to improve outcome after spinal cord injury", University of California San Francisco, 1 page, 2012.
Gertz, et al. "Transplantation of inhibitory neuron precursors to improve outcome after spinal cord injury", University of California San Francisco, Abstract, 2 pages, 2012.
Gotiinger, et al., Suppression of kindled seizures by paracrine adenosine release from stem cell-derived brain implants, Epilepsia, 2005, vol. 46, noB, pp. 1162-1169.
Grothe, et al., The physiological and pharmacological role of basic fibroblast growth factor in the dopaminergic nigrostriatal system, Brain Research Reviews, 54:80-91,2007.
Horiguchi, et al., Neural precursor cells derived from human embryonic brain retain regional specificity., Journal of Neuroscience Research, vol. 75, Issue 6, pp. 817-824, Mar. 15, 2004.
Humes (2005) "Stem cells: the next therapeutic frontier" Trans Am Clin Climatol Assoc 116:167-183.
Isacson et al. (1984) Functional neuronal replacement by grafted striatal neurons in the ibotenic acid-lesioned rat striatum, Nature, 311:458-460.
Jacoby, et al., Long-term survival of fetal porcine lateral ganglionic eminence cells in the hippocampus of rats, J Neurosci Res. Jun. 15, 1999;56(6):581-594.
Kordower et al. (1996) "Functional fetal nigral grafts in a patient with Parkinson's disease: chemoanatomic, ultrastructural, and metabolic studies" J Comp Neurol 370:203-230.
Lavdas et al. (1999) The medial ganglionic eminence gives rise to a population of early neurons in the developing cerebral cortex J Neurosci 99(19):7881-7888.
Lawerence, et al., Parvalbumin-, calbindin-, and calretinin-immunoreactive hippocampal interneuron density in autism, Acta Neurol Scand., 121 (2):99-1 08; Feb. 2010.

Loscher et al. (1998) "Seizure suppression in kindling epilepsy by grafts of fetal GABAergic neurons in rat substantia nigra" J Neurosci Res 51 :196-209.
Liu et al. "Medial ganglionic eminence-like cells derived from human embryonic stem cells correct learning and memory deficits", Nature Biotechnology, 31 :440-44 7, 2013.
Liu et al. (2013) "Directed differentiation of forebrain GABA interneurons from human pluripotent stem cells" Nature Protocols, 8(9):1670-1679.
Marin, et al. (2001) "A long, remarkable journey: tangential migration in the telencephalon" Nat Rev Neurosci 2 (11 ):780-790.
Marsala et al. (2004) "Spinal implantation of hNT neurons and neuronal precursors: graft survival and functional effects in rats with ischemic spastic paraplegia" Eur J Neurosci 20(9):2401-2414.
Mizuseki, et al. Generation of neural crest-derived peripheral neurons and floor plate cells from mouse and primate embryonic stem cells. PNAS, 2003, vol. 100, No. 10, pp. 5828-5833.
Montoya et al. (1989) "Effects of nigral and striatal grafts on skilled forelimb use in the rat" In Progress in Brain Research, 82:459-466.
Mostoufi et al. (2005) Spasticity and its management Pain Management Rounds 2(5):1-6.
Nadarajah, et al., Ventricle-directed migration in the developing cerebral cortex, Nat Neurosci—Mar. 1, 2002; 5(3): 218-224.
Nakao et al. (1996) "DARPP-32-rich zones in grafts of lateral ganglionic eminence govern the extent of functional recovery of in skilled paw-reaching in an animal model of Huntington's disease" Neuroscience, 74:959-970.
Nery et al. (2002) The caudal ganglionic eminence is a source of distinct cortical and subcortical cell populations Nat Neurosci 5( 12): 1279-1287.
Olsson, et al., Extensive migration and target innervation by striatal precursors after grafting into the neonatal striatum, Neuroscience. Jul. 1997;79{1 ):57-78.
Olsson, et al., Projection neurons in fetal striatal transplants are predominantly derived from the lateral ganglionic eminence, Neuroscience, vol. 69, Issue 4, Dec. 1995, pp. 1169-1182.
Ouellette et al. (2000) "The establishment of telomerase-immortalized cell lines representing human chromosome instability syndromes" Huma Molecular Genetics, 9:403-411.
Rao (2007) "Strategies for promoting anti-seizure effects of hippocampal fetal cells grafted into the hippocampus of rats exhibiting chronic temporal lobe epilepsy" Neurolbiol Dis 27(2): 117-132.
Ratte, et al., Selective Degeneration and Synaptic Reorganization of Hippocampal Interneurons in a Chronic Model of Temporal Lobe Epilepsy, Adv Neurol. 97:69-76, 2006.
Reutens (1997) "Results of surgical treatment in temporal lobe epilepsy with chronic psychosis" Brain 120(11 ):1929-1936.
Ross, et ai.,Transplantation of M213-20 cells with enhanced GAD67 expression into the inferior colliculus alters audiogenic seizures, Experimental neurology, 2002, vol. 177, No. 1, pp. 338-340.
Ruschenschmidt, et al., Functional properties of ES cell-derived neurons engrafted into the hippocampus of adult normal and chronically epileptic rats, Epilepsia, 2005, vol. 46, pp. 174-183.
Schwartz et al. (2003) "Feasibility of Interneuron Transplantation in the Treatment of Chronic Seizures in the Rat" Program No_ 533.18_ 2003 Neuroscience Meeting Planner_ New Orleans, LA: Society for Neuroscience.
Shields, et ai."Spared Nerve Injury Model of Neuropathic Pain in the Mouse: A Behavioral and Anatomic Analysis", The Journal of Pain, vol. 4, No. 8, pp. 465-470, 2003.
Sussel, et al. Loss of Nkx2.1 homeobox gene function results in a ventral to dorsal molecular respecification within the basal telencephalon: evidence for a transformation of the pallidum into the striatum. Development, (1999) 126, 3359-3370.
Tabar, et al., Migration and differentiation of neural precursors derived from human embryonic stem cells in the rat brain., Nat Biotechnol. May 2005;23(5):601-606.
Tande, et al., New striatal dopamine neurons in MPTP-treated macaques result from a phenotypic shift and not neurogenesis, Brain, 129, 1194-1200, Feb. 2006.
The Associated Press, Pig cells transplanted into brain of epilepsy patient, Copyright © 1998 The Standard-Times.

(56) References Cited

OTHER PUBLICATIONS

Thompson, et al., Embryonic Stem Cell Lines Derived from Human Blastocysts., Science Nov. 6, 1998: vol. 282. No. 5391, pp. 1145-1147.

Thompson, et al., Transplants of cells engineered to produce GABA suppress spontaneous seizures, Epilepsia. Jan. 2004;45(1):4-12.

Thompson. Genetically engineered cells with regulatable GABA production can affect afterdischarges and behavioral seizures after transplantation into the dentate gyrus. Neuroscience. 2005;133(4):1029-37.

Watanabe, et al. A ROCK inhibitor permits survival of dissociated human embryonic stem cells. Nat Biotechnol. Jun. 2007;25(6):681-6.

Watanabe, et al., Directed differentiation of telencephalic precursors from embryonic stem cells., Nat Neurosci. Mar. 2005;8(3):288-296.

Watis, et al. (2000) "Embryonic donor age and dissection influences striatal graft development and functional integration in a rodent model of Huntington's disease" Exp Neurol163(1):85-97.

Wernig, et al. {2004) "Functional Integration of Embryonic Stem Cell-Derived Neurons In vivo" J Neurosci. 24 (22):5258-68.

White and Loscher (2014) "Searching for the Ideal Antiepileptogenic Agent in Experimental Models: Single Treatment Versus Combinatorial Treatment Strategies," Neurotherapeutics, 11:373.384.

Wichterle, et al. (1999) "Young neurons from medial ganglionic eminence disperse in adult and embryonic brain" Nat Neurosci 2(5):461-466.

Wichterle, et al. {2003) Permissive corridor and diffusible gradients direct medial ganglionic eminence cell migration to the neocortex. Proc Natl Acad Sci U S A. Jan. 21, 2003; 10 0(2):727-32.

Wichterle, et at. (2001) "In utero fate mapping reveals distinct migratory pathways and fates of neurons born in the mammalian basal forebrain" Development. 128(19):3759-3771.

Winkler (1999) "Intranigral transplants of GABA-rich striatal tissue induce behavioral recovery in the rat Parkinson model and promote the effects obtained by intrastriatal dopaminergic transplants" Exp Neurol 155(2): 165-186.

Xu, et al., Cortical Interneuron Fate Determination: Diverse Sources for Distinct Subtypes?, Cerebral Cortex, vol. 13, No. 6, 670-676, Jun. 2003.

* cited by examiner

Distribution of MGE transplant cells

AMELIORATING NERVOUS SYSTEMS DISORDERS

CROSS-REFERENCE TO RELATED APPLICATIONS

This application claims priority benefit to U.S. provisional application Ser. No. 61/050,980 filed on May 6, 2008, which application is incorporated herein by reference in its entirety.

STATEMENT AS TO FEDERALLY SPONSORED RESEARCH

This invention was made with government support under grant no. NS048528 awarded by the National Institutes of Health. The government has certain rights in the invention.

INTRODUCTION

Clinical management of conditions, diseases and injuries of the central and peripheral nervous system usually focus of the prevention of further neurological damage or injury rather than on the repair or replacement of the damaged neurological tissue (e.g., neurons). For example, treatment of spinal cord injury includes the prevention of additional spinal cord injury by physically stabilizing the spine through surgical and non-surgical procedures and by inhibiting the inflammatory response with steroidal therapy. Thus, there remains a pressing need for improved and effective treatments of the central and peripheral nervous system that are able to repair or replace damaged or injured neural tissue.

SUMMARY

In some embodiments, a method is provided for the treatment of a mammal having a neurological condition, disease, or injury comprising increasing the number of functional GABAergic interneurons at or near the site of the neurological disease, injury, or condition, wherein the functional GABAergic interneurons functionally integrate with endogenous neurons and restore balance to neuronal circuitry that is dysregulated in neurological conditions, diseases, or injuries. In some embodiments, the increase in the functional GABAergic interneurons is by transplantation using injections of MGE (medial ganglionic eminence) precursor cells. In some embodiments, the MGE precursor cells are able to migrate at least 0.5 mm from the transplantation site.

In some embodiments, the neurological condition, disease, or injury is a degenerative disease, genetic disease, acute injury, or chronic injury. In some embodiments, the neurological condition, disease, or injury comprises Parkinson's disease, epilepsy, spasticity, multiple sclerosis, stroke, spinal cord injury, brain injury, or chronic pain disorders.

In some embodiments, the neurological condition is epilepsy, wherein transplantation of MGE precursor cells result in at least a 10% reduction in spontaneous electrographic seizure activity. In some embodiments, the neurological condition is epilepsy, wherein transplantation of MGE precursor cells result in at least a 10% reduction in seizure duration. In some embodiments, the neurological condition is epilepsy, wherein transplantation of MGE precursor cells result in at least a 10% reduction in seizure frequency. In some embodiments, the neurological condition is epilepsy, wherein transplantation of MGE precursor cells result in at least a 10% reduction in required antiepileptic drug use.

In some embodiments, the neurological disease is Parkinson's disease, wherein transplantation of MGE precursor cells result in at least a 10% reduction in required anti-Parkinsonian drug use. In some embodiments, the neurological disease is Parkinson's disease, wherein transplantation of MGE precursor cells result in at least a 10% reduction in tremor at rest, rigidity, akinesia, bradykinesia, postural instability, flexed posture and/or freezing. In some embodiments, the neurological disease is Parkinson's disease, wherein the MGE cells transplanted into the striatum survive for at least 6 months.

In some embodiments, the neurological condition is spasticity, wherein transplantation of MGE precursor cells mitigates or obviates the need for intrathecal medication or surgery. In some embodiments, the neurological condition is spasticity, wherein transplantation of MGE precursor cells result in at least a 10% reduction in required antispasmodic drug use In some embodiments, the MGE precursor cells express a therapeutic protein or peptide, or neurotransmitter. In some embodiments, the therapeutic protein or peptide comprises a neurotrophin, a neuropoietic cytokine, a fibroblast growth factor (e.g., acidic and basic FGF), an inhibitory growth factor, or a cytokine useful in the treatment of infectious disease, brain tumors, or brain metastases.

In some embodiments, the MGE precursor cells are injected into the striatum, basal ganglia, dorsal ganglia, ventral horn, or lumbar theca. In some embodiments, the mammal does not require immunosuppressive therapy following transplantation.

All publications and patent applications mentioned in this specification are herein incorporated by reference to the same extent as if each individual publication or patent application was specifically and individually indicated to be incorporated by reference. Nothing cited herein is to be construed as an admission that the invention is not entitled to antedate such disclosure by virtue of prior invention.

recording. Panel C, graph 1 shows the percentage observed for behavioral seizure manifestations including forelimb clonus (Stage 3, S3) in control mice and in mice with phenobarbital (PB), carbamezepine (CBZ), MGE, and phenytoin (PHT). For mice grafted with MGE cells at P2, the percentage of animals exhibiting S3 seizures was reduced to ~50%. Panel C, graph 2 shows the latency to first seizure behavior for control mice and in mice with phenobarbital (PB), carbamezepine (CBZ), MGE, and phenytoin (PHT). For mice grafted with MGE cells at P2, the latency to first seizure behavior was unchanged from that of the control mice.

Figure 13:
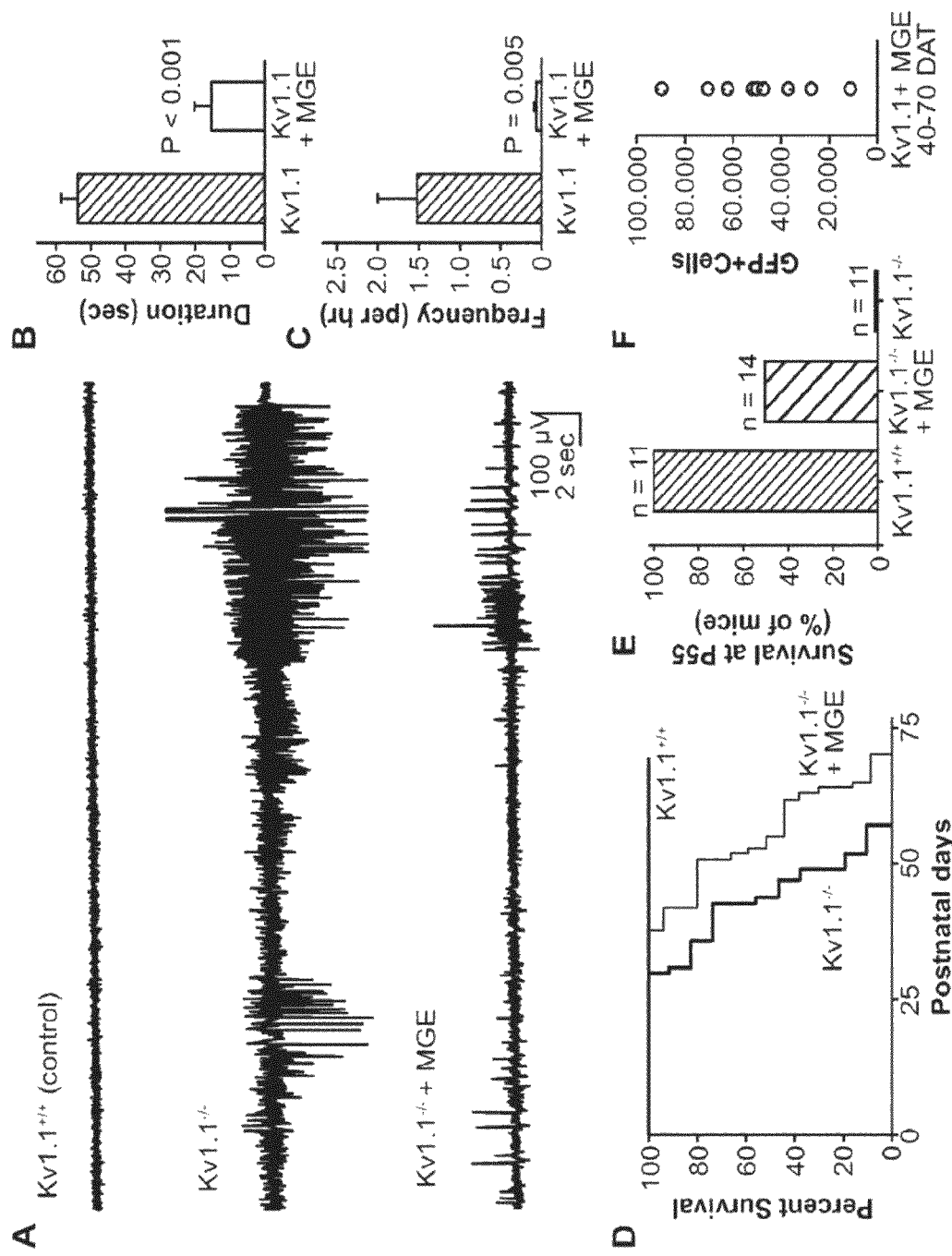

FIG. 13 is a collection of graphs as follows: Panel A shows video-electroencephalography (EEG) used to examine MGE transplant effects on spontaneous seizures in mice epilepsy model. Panel B shows the duration of the spontaneous seizures in mice epilepsy models with MGE transplants. Panel C shows the frequency of the spontaneous seizures in mice epilepsy models with MGE transplants. Panel D shows the Kaplan-Maier survival plots for postnatal days. Panel E shows the percentage of mice that survive at P55. Panel F shows new GFP cell density per brain in Kv1.1−/− mice that survive at P57.

DETAILED DESCRIPTION

While exemplary embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The practice of the present methods will employ, unless otherwise indicated, conventional techniques of cell biology, cell culture, molecular biology, transgenic biology, microbiology, recombinant DNA, and immunology, which are within the skill of the art. Such techniques are described in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

It must be noted that as used herein and in the appended claims, the singular forms "a," "an," and "the" include plural reference unless the context clearly dictates otherwise. Thus, for example, a reference to "a cell" includes a plurality of such cells and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, exemplary materials and methods are now described.

As common methods of administering the MGE precursor cells of the present disclosure to animals, particularly humans, which are described in detail herein, include injection or implantation of the MGE precursors cells into target sites in the animals, the cells of the disclosure can be inserted into a delivery device which facilitates introduction by, injection or implantation, of the cells into the animals. Such delivery devices include tubes, eg., catheters, for injecting cells and fluids into the body of a recipient animal. In a preferred embodiment, the tubes additionally have a needle, eg., a syringe, through which the cells can be introduced into the animal at a desired location. The MGE precursor cells can be inserted into such a delivery device, eg., a syringe, in different forms. For example, the cells can be suspended in a solution or embedded in a support matrix when contained in such a delivery device. As used herein, the term "solution" includes a pharmaceutically acceptable carrier or diluent in which the cells remain viable. Pharmaceutically acceptable carriers and diluents include saline, aqueous buffer solutions, solvents and/or dispersion media. The use of such carriers and diluents is well known in the art. the solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the present disclosure can be prepared as described herein in as a pharmaceutically acceptable carrier or diluent and, as required, other ingredients enumerated above, followed by filter sterilization.

The present disclosure also provides substantially pure MGE precursor cells that can be used therapeutically for treatment of various disorders. To illustrate, the MGE precursors of the disclosure can be used in the treatment or prophylaxis of a variety of conditions, diseases, or disorders. For instance, the MGE precursors can be used to produce populations of differentiated neurons for repair, replacement, or amelioration of damaged nervous system tissue for the treatment or prophylaxis of Parkinson's disease, epilepsy, schizophrenia, chronic pain disorders, neuropathic pain, multiple sclerosis, neuropathy, damage from traumatic injury, stroke, or ischemia and the like.

The invention will now be further described by way of reference only to the following non-limiting examples. It should be understood, however, that the examples following are illustrative only, and should not be taken in any way as a restriction on the generality of the invention described above. In particular, while the methods and compositions of the present disclosure are described in detail in relation to the use of mouse and rat cells, it will be clearly understood that the findings herein are not limited to these-types of cells, but would be useful growing any MGE precursor cell from any animal, including humans.

When the cells are implanted into the brain, stereotaxic methods will generally be used as described in Leksell and Jernberg, Acta Neurochir., 52:1-7 (1980) and Leksell et al., J. Neurosurg., 66:626-629 (1987), both of which are incorporated herein by reference. Localization of target regions will generally include pre-implantation MRI as described in Leksell et al., J. Neurol. Neurosurg. Psychiatry, 48:14-18 (1985), incorporated herein by reference. Target coordinates will be determined from the pre-implantation MRI.

Prior to implantation, the viability of the cells may be assessed as described by Brundin et al., Brain Res., 331: 251-259 (1985), incorporated herein by reference. Briefly, sample aliquots of the cell suspension (1-4 µl) are mixed on a glass slide with 10 µl of a mixture of acridine orange and ethidium bromide (3.4 g/ml of each component in 0.9% saline; Sigma). The suspension is transferred to a hemocytometer, and viable and non-viable cells were visually counted using a fluorescence microscope under epi-illumination at 390 nm combined with white light trans-illumination to visualize the counting chamber grid. Acridine orange stains live nuclei green, whereas ethidium bromide will enter dead cells resulting in orange-red fluorescence. Cell suspensions should generally contain more than about 98% viable cells.

In humans, injections will generally be made with sterilized 10 µl Hamilton syringes having 23-27 gauge needles. The syringe, loaded with cells, is mounted directly into the head of a stereotaxic frame. The injection needle is lowered to predetermined coordinates through small burr holes in the cranium, 40-50 µl of suspension are deposited at the rate of about 1-2 µl/minute and a further 2-5 minutes are allowed for diffusion prior to slow retraction of the needle. Frequently, two or more separate deposits will be made, separated by 1-3 mm, along the same needle penetration, and up to 5 deposits scattered over the target area can readily be made in the same operation. The injection may be performed manually or by an infusion pump. At the completion of surgery following retraction of the needle, the patient is removed from the frame and the wound is sutured. Prophylactic antibiotics or immunosuppressive therapy may be administered as needed.

In some embodiments of the present disclosure, the implanted cells may be transfected with a DNA sequence encoding a peptide. The peptide may be an enzyme which catalyzes the production of a therapeutic compound including the production of a neurotransmitter, e.g., the DNA could encode tyrosine hydroxylase which catalyzes the synthesis of dopamine that is effective in the treatment of Parkinsonism. The DNA may also encode a neurotrophic factor. Useful neurotrophic factors include the neurotrophins (e.g., NGF; brain-derived neurotrophic factor, BDNF; and neurotrophins NT-3 and NT-4/5); the neuropoietic cytokines (e.g., ciliary neurotrophic factor, CNTF); and the fibroblast growth factors (e.g., acidic and basic FGF). The DNA may also encode an inhibitory growth factor, or a cytokine useful in the treatment of infectious disease, brain tumors, or brain metastases.

Generally, the DNA sequence will be operably linked to a transcriptional promoter and a transcriptional terminator. The DNA sequence may also be linked to a transcriptional enhancer. Expression of the DNA in the implanted cells may be constitutive or inducible. A variety of expression vectors having these characteristics may carry the DNA for transfection of the cells, such as plasmid vectors pTK2, pHyg, and pRSVneo, simian virus 40 vectors, bovine papillomavirus vectors or Epstein-Barr virus vectors, as described in Sambrook et al., Molecular Cloning, A Laboratory Manual, Cold Spring Harbor Press, 1988, previously incorporated herein by reference. The vectors may be introduced into the cells by standard methods, such as electroporation, calcium phosphate-mediated transfection, polybrene transfection, and the like.

In some embodiments, the present disclosure is useful in the treatment of degenerative diseases. A degenerative disease is a disease in which the decline (e.g., function, structure, biochemistry) of particular cell type, e.g., neuronal, results in an adverse clinical condition. For example, Parkinson's disease is a degenerative disease in the central nervous system, e.g., basal ganglia, which is characterized by rhythmical muscular tremors, rigidity of movement, festination, droopy posture and masklike facies. Degenerative diseases that can be treated with the substantially homogenous cell populations of the present disclosure include, for example, Parkinson's disease, multiple sclerosis, epilepsy, Huntington's, dystonia, (dystonia musculmusculorum deformans) and choreoathetosis.

In some embodiments, the present disclosure is useful in the treatment of conditions caused by an acute injury. An acute injury condition is a condition in which an event or multiple events results in an adverse clinical condition. The event which results in the acute injury condition can be an external event such as blunt force or compression or an internal event such as sudden ischemia (e.g., stroke or heart attack). Acute injury conditions that can be treated with the substantially homogenous cell populations of the present disclosure include, for example, spinal cord injury, traumatic brain injury, brain damage resulting from myocardial infarction and stroke.

In some embodiments, the present disclosure provides methods of treating a human suffering from a neurological condition, comprising the step of administering to the human a substantially homogenous cell population of the present disclosure. "A neurological condition," as used herein, refers to any state of the nervous system (central or peripheral nervous system) which deviates in any manner from a normal nervous system or nervous system of a mammal, e.g., human, not affected by a neurological condition. The neurological condition can be a condition of the central (brain or spinal cord) or peripheral nervous system. The neurological condition can be, for example, the result or consequence of a disease, e.g., Parkinson's disease or multiple sclerosis, acute injury condition, e.g., stroke, brain injury, spinal cord injury, or a combination of disease and acute injury condition. Other neurological conditions which can be treated with the substantially homogenous population of cells of the present disclosure include, for example, chronic or intractable pain, primary brain tumors, or metastasizes.

In some embodiments, the administered cells comprise a substantially homogenous population. In some embodiments, the substantially homogenous population comprises cells wherein at least 25% of the cells become GABA expressing cells. In some embodiments, the substantially homogenous population comprises cells wherein at least 30%, 40%, 50%, 60%, 70%, 80%, 90%, 95%, or 99% of the cells become GABA expressing cells. In some embodiments, at least 25% of the cells comprising the substantially homogenous population of cells migrate at least 0.5 mm from the injection site. In some embodiments, at least 30%, 40%, 50%, 60%, 70%, 80%, 90%, 95%, or 99% of the cells comprising the substantially homogenous population of cells migrate at least 0.5 mm from the injection site. In some embodiments, the majority of the cells comprising the substantially homogenous population of cells migrate at least 1.0, 1.5, 2.0, 3.0, 4.0, or 5.0 mm from the injection site. In some embodiments, at least 25% of the substantially homogenous population of cells becomes functionally GABAergic interneurons. In some embodiments, at least 30%, 40%, 50%, 60%, 70%, 80%, 90%, 95%, or 99% of the cells become functionally GABAergic interneurons. In some embodiments, at least 25% of the substantially homogenous population of cells becomes functionally GABAergic interneurons that integrate with endogenous neurons. In some embodiments, at least 30%, 40%, 50%, 60%, 70%, 80%, 90%, 95%, or 99% of the substantially homogenous population of cells become functionally GABAergic interneurons that integrate with endogenous neurons.

In some embodiments, the substantially homogeneous population of cells becomes functional GABAergic interneurons and express one or more of the following: parvalbumin, calbindin, somatostatin, calretinin, neuropeptide Y, nitric oxide synthase, ChAT, NADPH diaphorase.

In some embodiments, the implanted functionally GABAergic interneurons increase the overall level of GABA-mediated synaptic inhibition in the host brain by at least 5%. In some embodiments, the implanted functionally GABAergic interneurons increase overall level of GABA-mediated synaptic inhibition in the host brain by at least 10%, 15%, 20%, 30%, 40%, 50%, 60%, 70%, 80%, 90%, or 95%. The increased inhibition can be monitored in patients by assaying for GABA levels in regions containing transplanted MGE cells.

In some embodiments, the functionally integrated transplanted interneurons represent at least 1% of the total number of the native striatal interneurons. In some embodiments, the functionally integrated transplanted interneurons represent at least 2%, 3%, 4%, 5%, 6%, 7%, 8%, 9%, 10%, 12%, 15%, 20%, 25%, or 30% of the total number of the striatal interneurons.

In some embodiments, the substantially homogenous cells secrete at least one neurotransmitter, therapeutic factor, cytokine and/or trophic factor. In some embodiments, the synthesis and secretion of at least one therapeutic factor, cytokine and/or trophic factor from the substantially homogenous population of cells of the present disclosure can protect surrounding cells near or distant from the site of transplantation from further damage as a consequence of the degenerative, acute injury or neurological condition. In some embodiments, the synthesis and secretion of at least one therapeutic factor, cytokine and/or trophic factor from the substantially homogenous population of cells of the present disclosure can also, or alternatively, promote regeneration of cells and tissues of the host, e.g., human suffering from a degenerative condition, acute injury, or neurological condition.

In some embodiments, the cell populations of the present disclosure have the capacity to respond to intrinsic signals, e.g., at the sites of transplantation, during migration, or at final migratory location, and exogenous cues to differentiate into neurons. The cell populations of the present disclosure can provide a readily available source of cells for use in treating animals, preferably mammals, and most preferably humans.

"MGE progenitor cell" or "MGE precursor cell," as used herein, refers to a cell obtained from a source, e.g., embryonic medial ganglionic eminence, umbilical cord blood, adult bone marrow, fat, skin, etc., that has substantially similar characteristics of a cell isolated from the MGE of E13.5 mouse fetuses, E14.5 rat fetuses, or develops into a cell with the substantially similar characteristics of a cell isolated from the MGE of E14.5 mouse fetuses. MGE progenitor cells can be isolated from human fetuses at 12-14 gestational weeks. A MGE progenitor cell can be a cell isolated from central nervous system tissue that is substantially similar to the MGE of E13.5 mice fetus or E14.5 rat fetus, a primary culture of cells grown from cells isolated from central nervous system tissue that is substantially similar to the MGE of E13.5 mice, E14.5 rat, or cells generated from other sources such as cell lines derived from embryonic or adult stem cells that are further differentiated to have substantially similar characteristics of cells isolated from the MGE of E13.5 mice or E14.5 rat.

In some embodiments, the cell line is produced by regulating the production of telomerase. In some embodiments, telomerase expression is forced by the expression of exogenous hTERT as detailed in Ouellette, M. M. et al. The establishment of telomerase-immortalized cell lines representing human chromosome instability syndromes. Human Molecular Genetics, 9:403-411, 2000. In some embodiments, the cell line is derived from pluripotent stem cells that are derived following reprogramming of adult somatic cells by somatic cell nuclear transfer as detailed by I. Wilmut, et al. Nature, 385, 810, 1997. In some embodiments, the cell line is derived from pluripotent stem cells that were derived following reprogramming of adult somatic cells by fusion with embryonic stem cells as described by Cowan, C. et al. Nuclear reprogramming of somatic cells after fusion with human embryonic stem cells. Science, 309, 1369-1372, 2005. In some embodiments, the cell line is derived from pluripotent stem cells that were derived following reprogramming of adult somatic cells by exposure to a defined set of reprogramming factors. In some embodiments, the reprogramming factors are OCT4, SOX2, NANOG, and LIN28 as detailed by Yu, J., et al. Induced pluripotent stem cell lines derived from human somatic cells. Science, 318, 1917-1920, 2007. In some embodiments, the reprogramming factors are Oct3/4, Sox2, Klf4, and c-Myc as detailed by Takahashi, K., et al. Induction of pluripotent stem cells from adult human fibroblasts. Cell, 131, 861-871, 2007.

Selected cells can be used directly from cultures or stored for future use, e.g., by cryopreserving in liquid nitrogen. If cyropreserved, MGE precursors must be initially thawed before placing the MGE precursors in a transplantation medium. Methods of freezing and thawing cryopreserved materials such that they are active after the thawing process are well-known to those of ordinary skill in the art.

In some embodiments, the present disclosure includes a pharmaceutical composition comprising a substantially homogeneous cell population of MGE precursors. In some embodiments, the pharmaceutical composition has at least about $10^5$ substantially homogeneous cells. In some embodiments, the pharmaceutical composition has at least about $10^6$, $10^7$, $10^8$, $10^9$, or $10^{10}$ substantially homogeneous cells. The cells comprising the pharmaceutical composition can also express at least one neurotransmitter, neurotrophic factor, inhibitory factor, or cytokine.

The cells of the present disclosure can be, for example, transplanted or placed in the central, e.g., brain or spinal cord, or peripheral nervous system. The site of placement in the nervous system for the cells of the present disclosure is determined based on the particular neurological condition, e.g., direct injection into the lesioned striatum, spinal cord parenchyma, or dorsal ganglia. For example, cells of the present disclosure can be placed in or near the striatum of patients suffering from Parkinson's disease. Similarly, cells of the present disclosure can be placed in or near the spinal cord (e.g., cervical, thoracic, lumbar or sacral) of patients suffering from a spinal cord injury. One skilled in the art would be able to determine the manner (e.g., needle injection or placement, more invasive surgery) most suitable for placement of the cells depending upon the location of the neurological condition and the medical condition of the patient.

The substantially homogenous cells of the present disclosure can be administered alone or as admixtures with conventional excipients, for example, pharmaceutically, or physiologically, acceptable organic, or inorganic carrier substances suitable for enteral or parenteral application which do not deleteriously react with the cells of the present disclosure. Suitable pharmaceutically acceptable carriers include water, salt solutions (such as Ringer's solution), alcohols, oils, gelatins and carbohydrates such as lactose, amylose or starch, fatty acid esters, hydroxymethycellulose, and polyvinyl pyrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like which do not deleteriously react with the cells of the present disclosure.

When parenteral application is needed or desired, particularly suitable admixtures for the cells are injectable, sterile solutions, preferably oily or aqueous solutions, as well as suspensions, emulsions, or implants. In particular, carriers for parenteral administration include aqueous solutions of dextrose, saline, pure water, ethanol, glycerol, propylene glycol, peanut oil, sesame oil and polyoxyethylene-block polymers. Pharmaceutical admixtures suitable for use in the present disclosure are well-known to those of skill in the art and are described, for example, in Pharmaceutical Sciences (17th Ed., Mack Pub. Co., Easton, Pa.) and WO 96/05309 the teachings of both of which are hereby incorporated by reference.

The substantially homogenous population of cells can be used alone or in combination with other therapies when administered to a human suffering from a neurological condition. For example, steroids or pharmaceutical synthetic drugs can be co-administered with the cells of the present disclosure. Likewise, treatment of spinal cord injury can include the administration/transplantation of the cells of the present disclosure in a human whose spine has been physically stabilized.

The dosage and frequency (single or multiple doses) of the administration or transplantation of the cells to a human, including the actual number of cells transplanted into the human, can vary depending upon a variety of factors, including the particular condition being treated, e.g., degenerative condition, acute injury, neurological condition; size; age; sex; health; body weight; body mass index; diet; nature and extent of symptoms of the neurological condition being treated, e.g., early onset Parkinson's disease versus advanced Parkinson's disease; spinal cord trauma versus partial or complete severing of the spinal cord); kind of concurrent treatment, e.g., steroids; complications from the neurological condition; extent of tolerance to the treatment or other health-related problems. Humans with a degenerative condition, acute injury, or neurological condition can be treated of once or repeatedly with cells of the present disclosure, e.g., about $10^6$ cells, at the same or different site. Treatment can be performed monthly, every six months, yearly, biannually, every 5, 10, or 15 years, or any other appropriate time period as deemed medically necessary.

The methods of the present disclosure can be employed to treat neurological conditions in mammals other than human mammals. For example, a non-human mammal in need of veterinary treatment, e.g., companion animals (e.g., dogs, cats), farm animals (e.g., cows, sheep, pigs, horses) and laboratory animals (e.g., rats, mice, guinea pigs).

Parkinson's Disease

Parkinson's disease (PD) affects approximately 150 per 100,000 people in the United States and Europe. PD is characterized by motor impairment as well as cognitive and autonomic dysfunction and disturbances in mood. Four cardinal features of PD can be grouped under the acronym TRAP: Tremor at rest, Rigidity, Akinesia (or bradykinesia) and Postural instability. In addition, flexed posture and freezing (motor blocks) have been included among classic features of parkinsonism, with PD as the most common form. Existing treatments can attenuate the symptoms of PD but there is no cure. The motor symptoms of PD result primarily from the loss of dopamine containing neurons in the substantia nigra compacta (SNc) that extend axonal projections to the striatum and release dopamine (for review see (Litvan et al., 2007). The SNc and the striatum belong to the basal ganglia, a network of nuclei which integrate inhibitory and excitatory signals to control movement. Loss of SNc cells in PD reduces the amount of dopamine release into the striatum, producing a neurotransmitter imbalance that inhibits the output of the basal ganglia and produces hypokinetic signs (for review (DeLong and Wichmann, 2007).

The striatum is composed of three classes of neurons. Medium spiny neurons are the projection neurons of the striatum and account for 95% of the total number of striatal neurons. The medium spiny neurons are GABAergic, express calbindin and substance P, give rise to nearly all outputs from the striatum, and receive nearly all the synapses from brain structures that project into the striatum (Tepper and Bolam, 2004). A second class of neuron is the large cholinergic neuron or large spiny neuron that is an excitatory striatal interneuron that expresses the marker cholineacetyltransferase (Chat). Cholinergic interneurons modulate the sub- and supra-threshold responses of the medium spiny neurons to cortical and/or thalamic inputs (Tepper and Bolam, 2004). The third class of striatal neuron is the GABAergic inhibitory interneuron or small spiny neuron of the striatum. These cells account for approximately 1-2% of the total number of striatal neurons. There are three subtypes of GABAergic inhibitory interneuron, and each subtype can be identified by the co-expression of specific markers: GABAergic interneurons that express calretinin (CR); GABAergic interneurons that express parvalbumin (PV); and GABAergic interneurons that express somatostatin, NADPH-diaphorase, and NOS (Kawaguchi et al., 1995; Tepper and Bolam, 2004). The GABAergic interneurons are the main source of inhibition of medium spiny neurons (Koos and Tepper, 1999; Koos et al., 2004; Plenz and Kitai, 1998). Each of the three types of GABAergic interneurons produce a strong inhibitory postsynaptic potential in medium spiny neurons, the function of which is to influence the precise timing of action potential firing in either individual or ensembles of medium spiny neurons. Both excitatory and inhibitory striatal interneurons are important sites of action for neuromodulators in the neostriatum, and act in different but complementary ways to modify the activity of the medium spiny projection neurons (Tepper and Bolam, 2004).

Striatal projection neurons and interneurons originate from the embryonic primordium of the basal ganglia, the ganglionic eminences. Inhibitory projection neurons are believed to derive from the medial ganglionic eminence (MGE, (Anderson et al., 1997; Deacon et al., 1994; Olsson et al., 1995), and the cholinergic excitatory projection neurons are thought to derive from the lateral ganglionic eminence (LGE) (Olsson et al., 1998). Previous data indicate that the GABAergic interneurons may have mixed origins. The CR+ subclass of interneurons derives mostly from MGE, but as many as ten percent may be derived from the LGE (Marin et al., 2000). The PV+ subclass of interneurons is thought to derive entirely from MGE (Marin et al., 2000). Transplantation studies suggest that Som+ interneurons may originate from both the LGE and MGE (Olsson et al., 1998), although the expression pattern of the transcription factor Nkx2.1, which is required for the specification of MGE derivates, suggests that Som+ cells are derived only from the MGE (Marin et al., 2000). The embryonic MGE also produces a substantial number of neocortical interneurons that migrate long distances over a tangential pathway to the dorsal neocortex, where they mature into local circuit GABAergic interneurons (Anderson et al., 1999; Lavdas et al., 1999; Wichterle et al., 1999). MGE cells retain the capacity for dispersal and integration when grafted heterochronically into neonatal or adult brain (Grasbon-Frodl et al., 1997; Olsson et al., 1997; Wichterle et al., 1999), develop into mature neurons when re-transplanted into the embryonic MGE (Butt et al., 2005), and can significantly increase the levels of inhibition exerted on neocortical projection neurons when grafted into the neocortex (Alvarez-Dolado et al., 2006).

The most widely used treatment for PD is administration of the dopamine precursor, levodopa, which improves motor behavior but also produces undesirable side effects including dyskinesias. Surgical approaches have been developed that involve electrical stimulation or ablation of the motor thalamus, the subthalamic nucleus, or the globus pallidus. Additional therapeutic strategies have been based on restoring or increasing concentrations of dopamine in the basal ganglia through transplantation of adult or embryonic dopamine-releasing tissues or stem cells.

To treat the motor symptoms of Parkinson's disease produced by a reduction of dopaminergic input, a non-dopamine based strategy that modified the circuit activity in the basal ganglia was employed. MGE cells were transplanted into the striatum of rats treated with 6-hydroxydopamine (6-OHDA), a well-established model of PD. This treatment relies on the ability of MGE cells to migrate, functionally integrate, and increase levels of inhibition in the host brain after transplantation. Transplanted MGE cells migrated from the site of injection and dispersed throughout the host striatum. Most MGE transplant cells acquired a mature neuronal phenotype and expressed neuronal and GABAergic markers. In addition, the transplanted cells expressed a variety of markers that are characteristic of striatal GABAergic interneurons such as CB, CR, CB, and Som. Finally, the MGE transplant cells became physiologically mature, integrated into the host circuitry, and improved the motor symptoms of PD in the rat 6-OHDA model. These results indicate that the transplantation of GABAergic interneurons restores balance to neuronal circuitry that has been affected by neurodegenerative diseases such as PD.

Example 1

Materials And Methods

Figure 1:
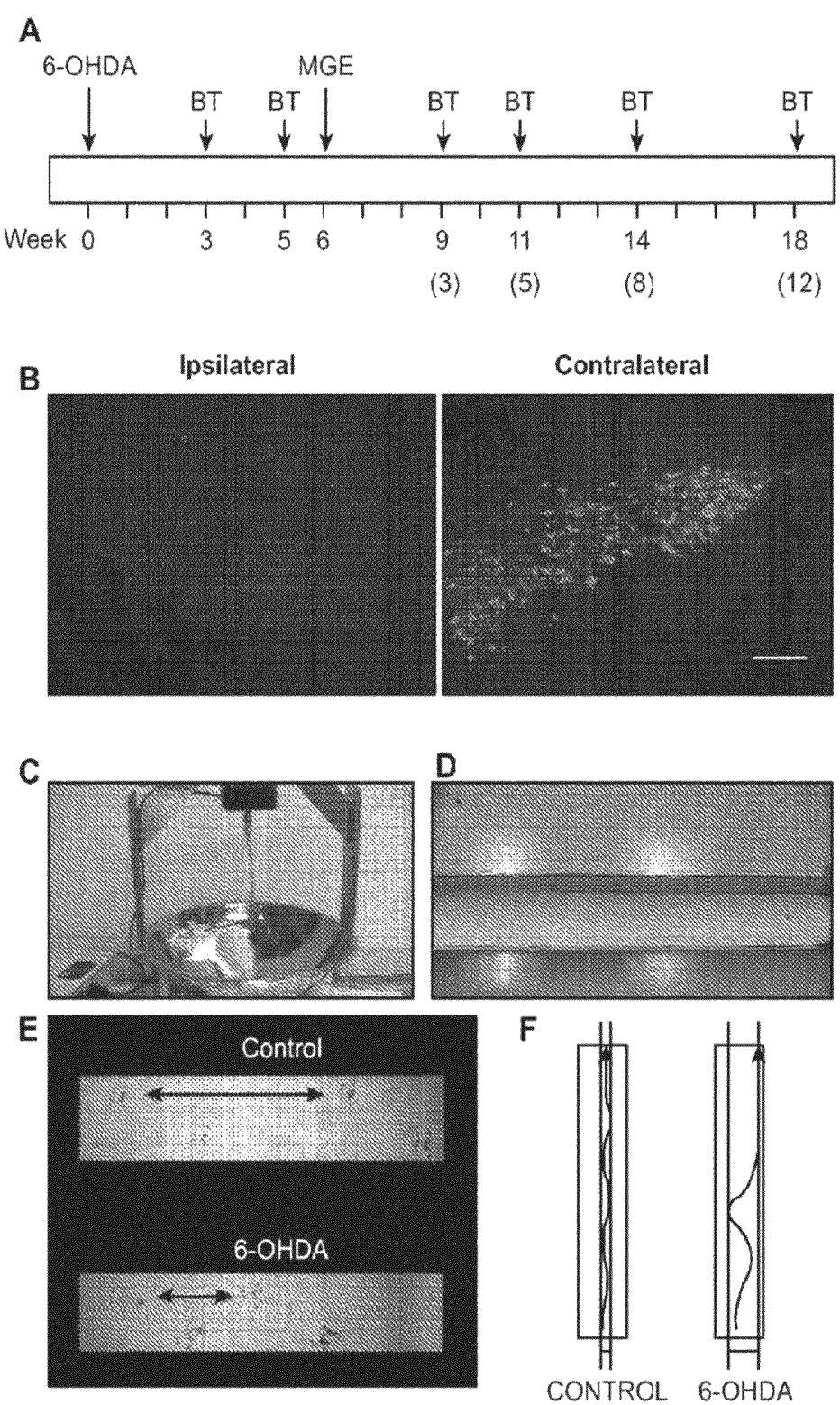
FIG. 1 is a collection of schematics as follows: Panel A. Experimental design. 6-OHDA-surgery was performed on day 1 and behavioral tests on weeks 3 and 5. If the rat showed parkinsonian behavior, it was injected with MGE cells on week 6. The behavioral tests were repeated on weeks 9, 11, 14 and 18. Unilateral lesion of the rat nigrostriatal projection. Tyrosine hydroxylase (TH) labels dopaminegic cells. The ipsilateral side to the injection did not show any stain for TH, while the contralateral side had numerous TH+ cells in the SNc, after 2 weeks. Drug-induced rotations were measured in an automated rotometer bowl. After intraperitoneal injection of apomorphine, the animals were fitted with a jacket that was attached via a cable to a rotation sensor, the animals were placed into the test bowl and the number of clockwise or counterclockwise rotations was recorded over a test period of 40 minutes. Rats were place into a runway. The floor of the runway was covered with paper. The rats were trained to run down the runway. At the start of each test, the animals' feet were dipped in black ink before being placed at the beginning of the runway. The length of stride was measure for each test. 6-OHDA length of stride was shorter than that of controls. Panel B. 6-OHDA rats tended to wander from side to side as they walked down the runway rather than follow a straight path. Scale bar: A=30 μm.

Experimental design 6-OHDA lesions were induced on experimental day 1 and performed behavioral tests on weeks 3 and 5. In rats selected for grafting, MGE cells were transplanted on week 6, and behavioral tests were repeated on weeks 9, 11, 14 and 18 (FIG. 1, Panel A). All animals were treated in accordance with protocols approved by the Institutional Animal Care and Use Committee at UCSF.

6-OHDA-model Unilateral lesions of the nigrostriatal projection in rats, using 6-OHDA, leads to the loss of dopaminergic cells in the SNc through retrograde transport, and loss of dopaminergic terminals in the striatum through axonal disruption (Berger et al., 1991). As a consequence, the distribution of D1 and D2 receptors is altered. Unilateral damage can result in bilateral changes in the SNc (Berger et al., 1991). Damage of the nigrostriatal pathway in rats is accompanied by a compensatory increase in the synthesis and release of dopamine from the dopaminegic terminals that remain (Zigmond et al., 1984). To evaluate the success of surgery, a subset of animals (n=5) were perfused 4 weeks after lesion and the SNc stained for tyrosine hydroxylase immunoreactivity (TH-IR), a limiting enzyme in the synthesis of dopamine, in order to label dopaminegic cells. In successful surgeries, the side of the SNc ipsilateral to the 6-OHDA injection did not show TH-IR, while the contralateral side had numerous TH+ cells (FIG. 1, Panel B). To evaluate the 6-OHDA surgeries in vivo, behavioral testing was performed (described below).

6-OHDA-surgery Adult female rats were anesthetized with ketamine (90 mg/Kg) and xylazine (7 mg/Kg), and when insensitive to pain, immobilized within a stereotaxic frame in flat skull position. A two-centimeter mid-sagittal skin incision was made on the scalp to expose the skull. The coordinates for the nigrostriatal bundle were determined based on the Paxinos and Watson adult rat brain atlas (Paxinos and Watson, 1982). A hole was drilled through the skull at the appropriate coordinates, and a glass capillary micropipette stereotaxically advanced so that the internal tip of the pipette was located within the nigro-striatal pathway. The micropipette had a 50 µm diameter tip and was filled with a solution of 6-OHDA, 12 gr/3 µl in 0.1% ascorbic acid-saline. The 6-OHDA was injected into the right nigro-striatal pathway at a rate of 1 µl/minute. The micropipette was kept at the site for an additional 4 minutes before being slowly withdrawn. The skin incision was closed with stainless steel wound clips. Each animal was injected with 6-OHDA on the right side only, producing hemi-Parkinsonian rats.

MGE transplant surgery Adult pregnant rats that carried the green fluorescent protein (EGFP) under the chick-beta actin promoter (Wistar-TgN (CAG-GFP, 184Ys, Rat Resource and Research Center) were anesthetized as described above. Fetuses were removed from the uterus at E14.5 and brains dissected under a microscope. The MGE was dissected from the forebrain in oxygenated artificial cerebrospinal fluid (aCSF, in mm: NaCl, 125; KCl, 2.5; MgCl2, 1; CaCl2, 2; NaPO4, 1.25; NaHCO3, 25; and glucose, 25; Sigma). Eight MGEs were used to prepare dissociated cells for each surgery. The MGE tissue was mechanically dissociated in the presence of 1% DNAse I in aCSF. Cells were centrifuged at 2× gravity for 2 minutes, and pellets dissociated in 5 µl of aCSF. Cells were injected immediately after dissociation. Three injections were performed along the rostro-caudal axis of the striatum, and cells were deposited at three delivery sites along the dorsal-ventral axis at each injection site, starting with the most ventral site first and then withdrawing the injection pipette dorsally to perform the second and third injections. 400 nl of cell suspension was injected at each delivery site, and a total of 3.6 µl of MGE cell suspension was injected in each striatum. One 300 nl injection was performed into the STN. The total number of transplanted cells were 252,390±7729 (n=3 rats).

Immunocytochemistry Rats were anesthetized as described above and perfused intracardially with 0.1M phosphate buffer saline (PBS) followed by 4% paraformaldehyde in PBS. The brains were removed and post-fixed 24 hours in the same paraformaldehyde at 4° C. Coronal 50 µm slices were prepared on a vibratome (Leica). Free-floating sections were blocked in 10% donkey serum (Gibco, Calif., USA), 0.1% triton X-100 (Sigma, Mo., USA) and 0.2% gelatin (Sigma, Mo., USA). Sections were incubated 24 hours in primary antibodies at room temperature. The primary antibodies were: anti-neuronal specific nuclear protein (mouse anti-NeuN, Chemicon), Gamma Aminobutryic Acid (rabbit anti-GAB A (1:1000, Sigma), Glutamic Acid Descarboxylase 67 (mouse anti-GAD, 1:1000, Abcam), GABA Transporter 1 (rabbit anti-GAT, 1:300, Abcam), CNPase (mouse anti-1:500, Abcam), Glial Fibrillary Acidic Protein (rabbit anti-GFAP, 1:1000; Sigma), Substance P (rabbit anti-SP, 1:2000, Chemicon), Somatostatin (mouse anti-Som, 1:100, Abcam), Nitric Oxide Synthase (rabbit anti-NOS, 1:100, Abcam), Choline Acetyltransferase (goat anti-Chat, 1:100; Chemicon), Tyrosine Hydroxylase (mouse anti-TH, 1:1000, Boehringer Mannheim Biochemica), Parvalbumin (mouse anti-PV, 1:1000, Chemicon), Calretinin (mouse anti-CR, 1:1000; Chemicon), Calbindin (mouse anti-CB, 1:2000; Swant, Bellinzona, Switzerland), Synaptophysin (mouse anti-Synaptophysin, 1:200, Sigma), Dopamine- and cAMP-regulated Protein (rabbit anti-DARPP 32, 1:50, Abcam), Dopamine Transporter (rat anti-DAT, 1:500, Abcam), Vesicular Monoamine Transporter 2 (rabbit anti-VMAT, 1:1000, Abcam), Dopamine Receptor 1 (rabbit anti-DR1, 1:2000, Abcam), Dopamine Receptor 2 (rabbit anti-DR2, 1:500, Abcam), and green fluorescent protein (chicken anti-GFP, 1:1000, Abcam). Sections were rinsed and incubated in the appropriate secondary antibody: Cy2, Cy3 or Cy5 conjugated polyclonal anti-mouse/goat/rabbit antibodies (1:100, Jackson Laboratories, ME, USA). Tissue was rinsed and mounted on coated glass slides and cover-slipped with an aqueous mounting medium (Aquamount; Lerner, Pa., USA). Confocal microscopy was performed on an Olympus Fluoview confocal laser scanning microscope and analysis performed in Fluoview v.3.3 (Olympus). The first antibody was omitted as a control for each immunostaining experiment.

Cell quantification The survival of MGE cells after transplantation, and the percentage of transplanted MGE cells that expressed cell specific markers were quantified through confocal microscopy. Brains were perfused as described above at three days, one week, two weeks, three weeks, four weeks, eight weeks and 12 weeks after transplantation. Brains were cut into 50 µm thick coronal sections as described above. The number of MGE cells that survived transplantation was estimated by quantifying the number of cells in every third 50 µm thick section throughout the rostro-caudal axes of the brain, and multiplying this number by three. The percentage of MGE transplanted cells that expressed cell-type specific markers was calculated using at least three animals for each marker (n=27 total animals analyzed). MGE cells were counted in three coronal sections: one section at the level of a MGE cell transplantation, a second section 300 µm rostral to the injection, and a third section 300 µm caudal to the site of injection. The total number of GFP+ MGE cells in each section were counted and the percent that were positive for NeuN, GABA, GAD, GAT, CR, CB, PV, Som, Substance P, NOS, Chat, CNPase, and synaptophysin were quantified at three time points after transplantation (four, eight and 12 weeks).

Electrophysiology Coronal slices for electrophysiological recordings of GFP+ MGE transplanted cells were prepared as described previously (Noctor et al., 2008). Briefly, brains were sectioned at 400 µm with a vibratome (Leica) in ice-chilled artificial cerebrospinal fluid (aCSF) bubbled continuously with 95/5% O2/CO2. containing (in mM): NaCl 125, KCl 5, NaH2PO4 1.25, MgSO4 1, CaCl2 2, NaHCO325, and glucose 20, pH 7.4, at 25° C., 310 mOsm/l. Tissue slices were allowed to rest for one hour before recording. Slices were transferred to a recording chamber on an Olympus BX50WI upright microscope and were perfused with aerated aCSF. GFP+ cells were identified under epifluorescence and recordings performed using an EPC-9 patch-clamp amplifier (Heka Electronics) controlled by an Apple computer running Pulse v8.0 (Heka). Glass recording electrodes (7-10 MΩ) were filled with (in mM): KCl 130, NaCl 5, CaCl2 0.4, MgCl2 1, HEPES 10, pH 7.3, EGTA 1.1, to which 500 µM Alexa 594-conjugated biocytin (Molecular Probes) was added to identify recorded cells. Epifluorescent images of the recorded cells were collected using Scion Image, and arranged using Photoshop. Electrophysiological responses were measured and analyzed using Pulse, and traces were arranged using Igor Pro (Wavemetrics), and Freehand (Macromedia).

Behavioral tests Behavioral tests were performed 3 and 5 weeks after 6-OHDA surgery and 3, 5, 8 and 12 weeks after MGE cell transplants. All animals were cared for according to protocols approved by the Institutional Animal Care and Use Committee at UCSF.

Rotational behavior: Each rat was injected with the dopamine agonist apomorphine (0.05 mg/kg, IP) to produce contralateral rotational behavior in 6-OHDA treated rats. Drug-induced rotations were measured in an automated rotometer bowl 28 cm in diameter×36 cm high (Columbus Instruments, Ohio, Brain Research, 1970, 24:485-493). After intraperitoneal injection of apomorphine, the animals were fitted with a jacket that was attached via a cable to a rotation sensor. The animals were placed in the test bowl and the number and direction of rotations was recorded over a test period of 40 minutes. This test was administered to each rat to verify and quantify the efficacy of the intracranial 6-OHDA-infusion (FIG. 1, Panel C). Apomorphine stimulates dopaminergic receptors directly, preferentially on the denervated side due to denervation induced dopamine receptor supersensitivity, causing contralateral rotation (Creese et al., 1977; Ungerstedt, 1971; Ungerstedt and Arbuthnott, 1970). There is a threshold of SNc damage that must be reached in order to produce maximal rotation behavior after apomorphine administration (Hudson et al., 1993). The abnormal behavior of hemi-Parkinsonian rats is directly related to the amount of DA cell loss. When there is less than 50% dopamine depletion in the striatuma significant change in rotation behavior after apomorphine injection was not observed, due to compensatory mechanisms in the striatum. For the grafting experiment only those 6-OHDA rats that rotated at least four times more to the contralateral than to the ipsilateral side of the injection were selected.

Stride test: The test animal was placed on a runway 1 m long and 33 cm wide with walls 50 cm high on either side. The runway was open on the top, and was situated in a well-lit room. A dark enclosure was placed at one end of the runway, and rats were free to enter the enclosure after traversing the runway. Rats were trained to run down the runway by placing them on the runway at the end opposite to the dark enclosure. The practice runs were repeated until each rat ran the length of the runway immediately upon placement in the runway. The floor of the runway was covered with paper. At the start of each test, the animals' rear feet were dipped in black ink before being placed at the beginning of the runway. The test twice was repeated for each rat and the length of stride for each test was measured to obtain an average stride length for each rat. The average stride length was compared across groups. 6-OHDA rats display impairments in the posture and movement of the contralateral limbs. They compensate by supporting themselves mainly on their ipsilateral limbs, using the contralateral limb and tail for balance, and by disproportional reliance on their good limbs to walk. The good limbs are responsible for both postural adjustments and forward movements and they shift the body forward and laterally (Miklyaeva, 1995). The bad limb produces little forward movement, and as a consequence the length of step is shorter in 6-OHDA rats than in control rats (FIG. 1, Panels D,E).

Width of the path test: Normal control rats ran straight down the runway to the enclosure at the end. In 6-OHDA rats, however, the limb impairment produced a wandering path that zig-zagged from side to side, and as a consequence the pathway followed by the 6-OHDA rats was wider than normal. The maximum width of the path for control and experimental groups were compared (FIG. 1, Panel F).

Open Field Test: An Open Field 16×16 Photobeam System with Flex-Field software (SD Instruments) was used to record the complete coordinates of a rat's movements within an acrylic enclosure (40 cm wide, 40 cm deep and 37.5 cm high). Each animal was placed in the center of the enclosure at the start of the test and allowed to freely explore the apparatus for 5 minutes. The movement of the rat interrupts the laser photobeams. The Flex-Field software recorded units of movement, which were represented by the number of entries into each of the 256 square zones of the open field, and the amount of time spent at each point. At the end of the experiment the movement of each rat during the 5 minutes period was represented as units of movement, and by a zone map that traced the path followed by the rat in the open field.

Results

MGE Cells Survived Up to One Year after Transplant into the Adult Striatum

To determine if MGE cells survive in the adult striatum, 6-OHDA rats transplanted into the striatum with MGE cells carrying the GFP reporter gene were sacrificed at various times after transplant. Of the approximately 250,000 cells injected, most died during the first 3 weeks after transplant. By week 4, approximately 1% (2,613±156) of the transplanted cells were present. These cells, however, persisted, and the number of surviving transplanted cells did not decrease further at 8 and 12 weeks and for up to one year after transplantation. To determine if the transplanted MGE cells continue to proliferate after transplantation the fixed tissue was labeled with Ki67, a marker expressed by dividing cells. Ki67+ MGE cells were not found at four, eight and 12 weeks after transplantation, indicating that even if the MGE cells were initially proliferative, they had ceased dividing within four weeks after transplantation.

Transplanted MGE Cells Migrate Throughout the Striatum

Figure 2:
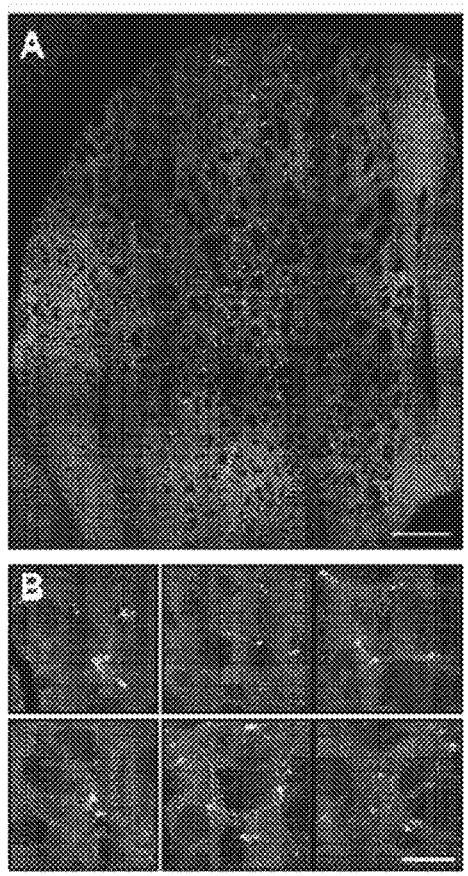
FIG. 2 is a collection of images as follows: Panel A. Striatum 4 weeks after transplant. The transplanted GFP- MGE cells migrated 2 to 2.5 mm in all the directions from the site of injection. The cells covered the whole span of the striatum but never migrated outside it. Panel B. Transplanted cells 8 weeks after transplant had a fully mature appearance, an oblong body shape and numerous processes that extended up to 50 µm, and occupied the whole striatum even in areas far away from cellular GFP-MGE somas. The processes intermingled and seemed to contact one another. Scale bars: A=0.5 mm; B=25 µm.

The GFP reporter gene expression in the MGE transplant cells allowed for the examination of the morphology and behavior of the surviving MGE cells. At 3 and 7 days post-transplant, GFP+ cells had the classical morphology of migrating neurons, including a simple bipolar shape and a leading process. At two weeks post transplant many of the transplanted cells had migrated up to 2.0 to 2.5 mm in all the directions from the site of transplantation, and some of the transplanted cells had migrated up to 3.5 mm. At two weeks post transplant the cells appeared more mature and displayed abundant neuritic processes. The vast majority, if not all GFP+ cells migrated within the striatum and did not migrate outside its borders (FIG. 2, Panel A).

After 4 weeks, the transplanted MGE cells had a fully mature appearance. Most of them had an oblong cell body and numerous processes that extended at least 50 $\mu$m. Each process extending from the transplanted cell gave rise to second, third and fourth order processes. Eight and 12 weeks after transplantation most GFP+ cells were found within 2.5 mm of the injection. Grafted cells had very extensive and ramified processes that could be observed as GFP+ fibers or puncta throughout the transplanted striatum. Therefore, GFP+ transplant cell processes appear to occupy the entire striatum, including areas remote from the injection sites. (FIG. 2, Panel B).

Most Transplanted MGE Cells Transformed into Inhibitory GABA+ Cells

The fate of the transplanted MGE cells was examined by quantifying the percentage of MGE cells that expressed cell-specific markers at four, eight, and 12 weeks after transplant. At four weeks after transplantation, the majority of the transplanted MGE cells had differentiated into neurons since 75% expressed the mature neuronal marker NeuN+ (75±6%, n=676). Most of the transplanted cells also expressed markers of GABAergic neurons, including GABA (75±4%, n=294), the GABA synthesizing enzyme GAD (60±11%, n=382), and the GABA transporter GAT (50±9%, n=380, see FIG. 3). These data indicate that the majority of MGE transplanted cells became GABAergic neurons.

Figure 3:
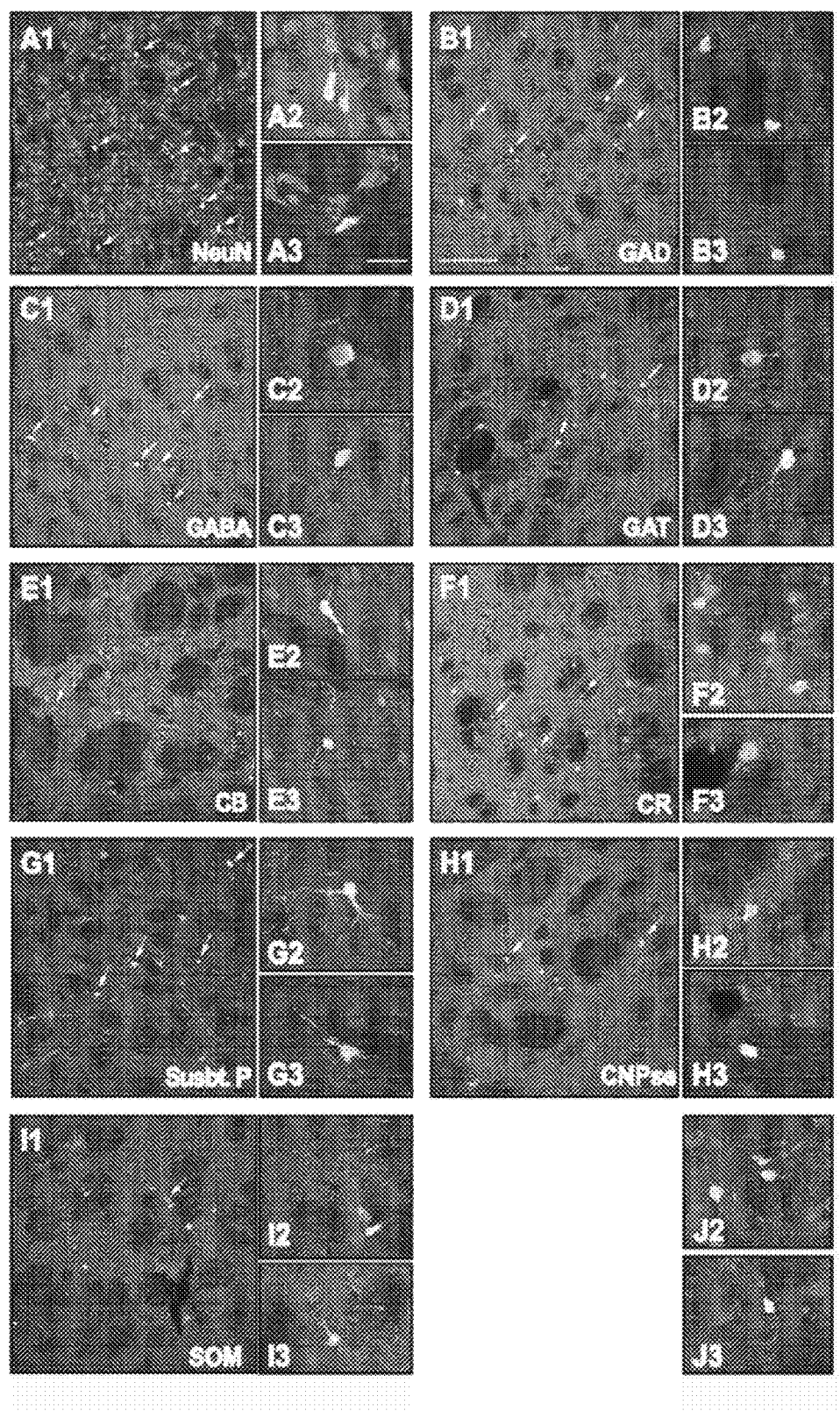
FIG. 3 is a collection of images as follow, illustrating that most (3:1) MGE cells showed interneuronal fate when transplanted into the adult striatum. Four weeks after transplant, MGE-cells expressed the mature neuronal markers NeuN+ (A, 75±6%), GAD (B, 60±11%), GABA+ (C, 75±4%), GAT (D, 50±9%), CB (E, 24±7%), CR (F, 8.3±0.5%), Substance P (G, 6±2%), CNPase (H, 25%±4), Somatostatin (I, 1±0.5%) and Chat. Scale bars: B1=10 µm and applies to Panels A1, C1, D1, E1, F1, G1, H1, I1, and J1; A3=30 µm and applies to Panels A2, B1, B2, C1, C2, D1, D2, E1, E2, F1, F2, G1, G2, H1, H2, I1, I2, J1, and J2.

Next, the transplanted cells were examined for the expression of additional markers that are typical of striatal neurons in the adult brain. Some of the GFP+ cells expressed markers of striatal interneuron subtypes such as the calcium binding protein calretinin (CR, 8.3±0.5%, n=473) and parvalbumin (PV, 0.5±0.5%, n=320), Som (1±0.5%, n=300), or NOS (1±0.7%, n=337). A small percentage of the transplanted MGE cells expressed the cholinergic interneuron marker Chat, which is expressed by striatal excitatory interneurons. Some of the transplanted GFP+ MGE cells expressed markers that are typical of striatal inhibitory projection neurons such as CB (24±7%, n=300) and Substance P (6±2%, n=193) (for review (Tepper and Bolam, 2004) (FIG. 3).

Transplanted cells were also examined for expression of markers that are related with dopamine synthesis, but none of the observe transplanted cells expressed VMAT or DAT. Additionally, DARPP 32 expression, a marker of adult medium spiny projection neurons, was not expressed by MGE cells. Together these data indicate that most MGE cells transplanted into adult striatum differentiate into local GABAergic interneurons and express a range of cell specific markers that are normally expressed in the adult rat striatum.

The pattern of marker expression of grafted cells was largely preserved at 8 and 12 weeks, except for the number of Som expressing cells that rose slightly at 12 weeks after transplantation (10±3%, n=343). In contrast, by 12 weeks after transplantation, the number of MGE cells that expressed the calcium binding proteins was reduced (CR, 2±1%, n=258; CB, 2±1.5% n=270; PV, 0%, n=136). Interestingly, the transplantation of the MGE cells temporarily induced strong expression of CR and CB by host cells surrounding the injection site. The strong expression at four weeks after transplantation, was not present at 8 or 12 weeks. Host cells in the control animals that received only vehicle did not express CR or CB, indicating that the expression was likely due to presence of the grafted cells.

Approximately, one fourth of the grafted MGE cells (25±4%) were NeuN-negative. These cells stained positive for the myelin protein, CNPase, indicating that a subpopulation of the grafted cells differentiated into oligodendrocytes. None of the cells transplanted into the striatum expressed GFAP suggesting that grafted cells did not differentiate into astrocytes. The ratio of neuronal to glial cells (3:1) was maintained at 8 and 12 weeks post transplantation.

MGE Transplanted Cells Integrated into Striatal Circuitry

Figure 4:
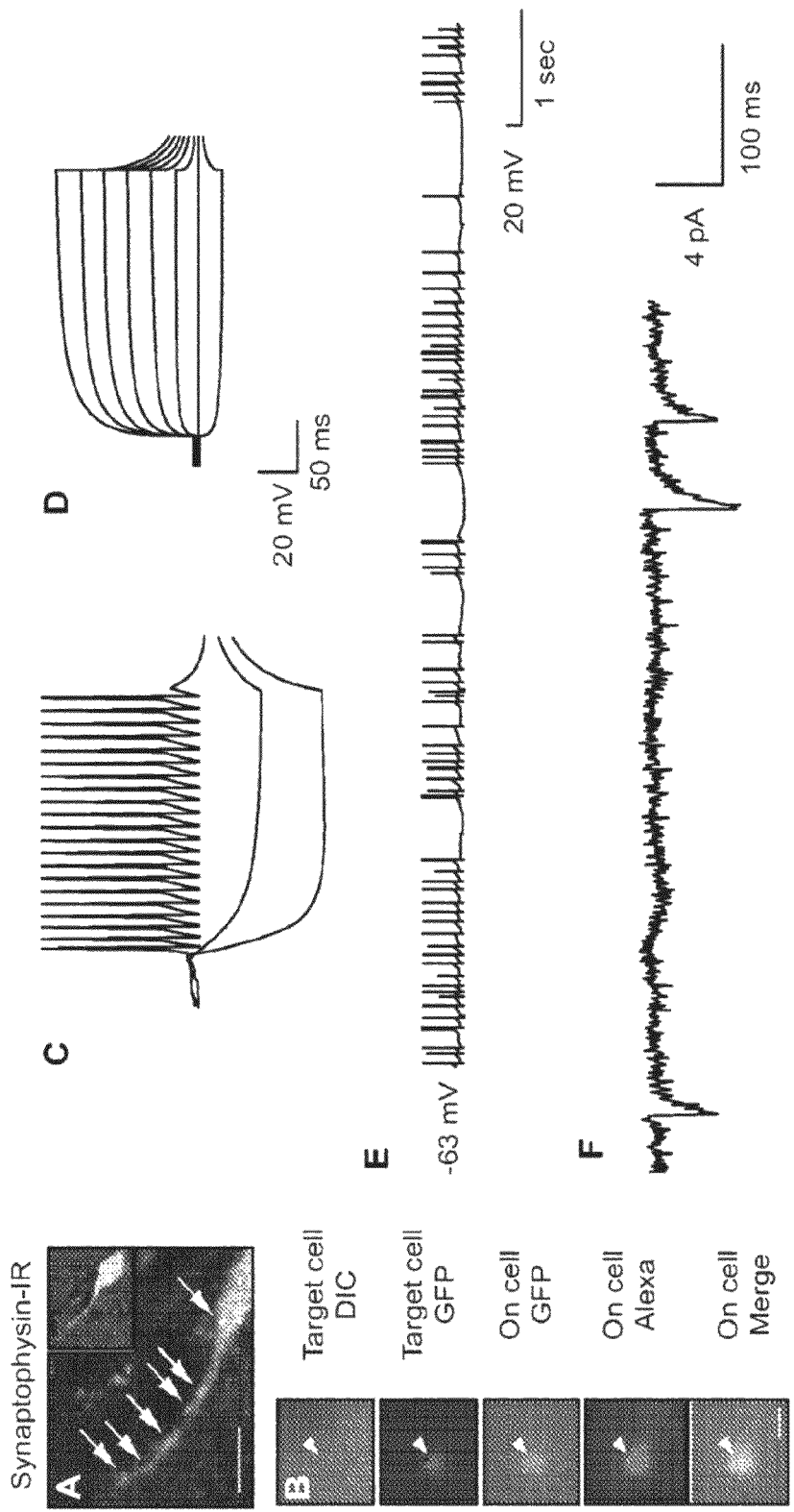
FIG. 4 is a collection of graphs and images showing that MGE cells transplanted into the striatum retain the basic membrane properties that are characteristics of cortical interneurons Panel A. 67% of the MGE cells expressed synaptophysin in their processes (white arrows). Panel B. Alexa-594 was included in the fill solution of the glass microelectrode to determine whether the obtained whole-cell recordings were from the targeted GFP-expressing MGE transplant cells. Panel C. MGE cells fired repetitive non-accommodating action potentials with large after hyperpolarizations when stimulated with a series of depolarizing currents, as is common for MGE derived interneurons. Panel D. Some of the transplanted MGE cells (n=2/13) did not possess neuronal membrane properties and did not fire action potentials. Panel E. MGE transplant cells fired spontaneous action potentials, and Panel F. exhibited spontaneous synaptic currents at a frequency of 1.1 psc/s, which was similar to that recorded from host cells (1.0 psc/s). Scale bars: A=3 µm; B=5 µm.

The MGE transplanted cells were examined for the establishment of synaptic connections in the striatum and functionally integratation. At four weeks after transplantation, 67±3% of the GFP+ MGE cells (n=193) expressed synaptophysin puncta along their processes, indicating the presence of synapses (FIG. 4, Panel A). Electrophysiological recordings provided further evidence that the MGE cells became functionally integrated into the host striatum. Whole-cell patch-clamp recordings were obtained from GFP+ MGE cells 20 weeks after transplantation to examine their basic membrane properties (n=13 cells). Alexa-594 dye was included in the patch electrodes to confirm that recordings were obtained from targeted GFP-expressing transplant cells (FIG. 4, Panel B). The recordings demonstrated that most of the transplanted MGE cells became functionally mature neurons (11/13 cells). The neuronal cells had a resting membrane potential of 65.9±5.1 mV. In voltage clamp recordings, a series of depolarizing voltage steps elicited voltage gated inward currents characteristic of neurons (FIG. 4, Panel C). In current clamp recordings, a series of depolarizing current steps elicited mature action potentials (APs) with a spike amplitude of 69.1±4.6 mV, and large after-hyperpolarizations of 14.5±2.9 mV (FIG. 4, Panel D). In addition, the transplanted MGE cells fired repetitive non-accommodating APs, (FIG. 4, Panel D) and trains of spontaneous APs (FIG. 4, Panel F). The membrane properties of the transplanted cells were consistent with that of MGE derived interneurons in the cerebral cortex (Alvarez-Dolado et al., 2006; Butt et al., 2005), and with the membrane properties recorded from host striatal interneurons (Kawaguchi, 1993).

Indeed, some of the transplanted MGE cells fired APs at frequencies greater than 100 Hz, indicating a fast-spiking interneuron phenotype. The transplanted MGE cells also displayed evidence that they were receiving synaptic inputs. In voltage clamp recordings the GFP+ neurons exhibited spontaneous synaptic currents at a frequency of 1.1±0.2 Hz (FIG. 4, Panel G), which was similar to the frequency observed in recordings obtained from control host striatal cells (1.0±0.3 Hz, n=5 host cells). These results are consistent with those of Alvarez-Dolado et al. (Alvarez-Dolado et al., 2006), who showed that transplanted MGE cells increased the amount of GABAergic inhibition on host neocortical projection neurons. Two of the recorded GFP+ cells did not express voltage-dependent inward currents, and did not fire action potentials when stimulated with a series of depolarizing currents (FIG. 4, Panel E). These recordings were most likely obtained from the non-neuronal, CNPase+ population of transplanted cells, and are consistent with the membrane properties of mature glial cells in the cortex. Together these data support the conclusion that most transplanted MGE cells become inhibitory interneurons and are synaptically integrated into the host striatal circuitry.

Figure 5:
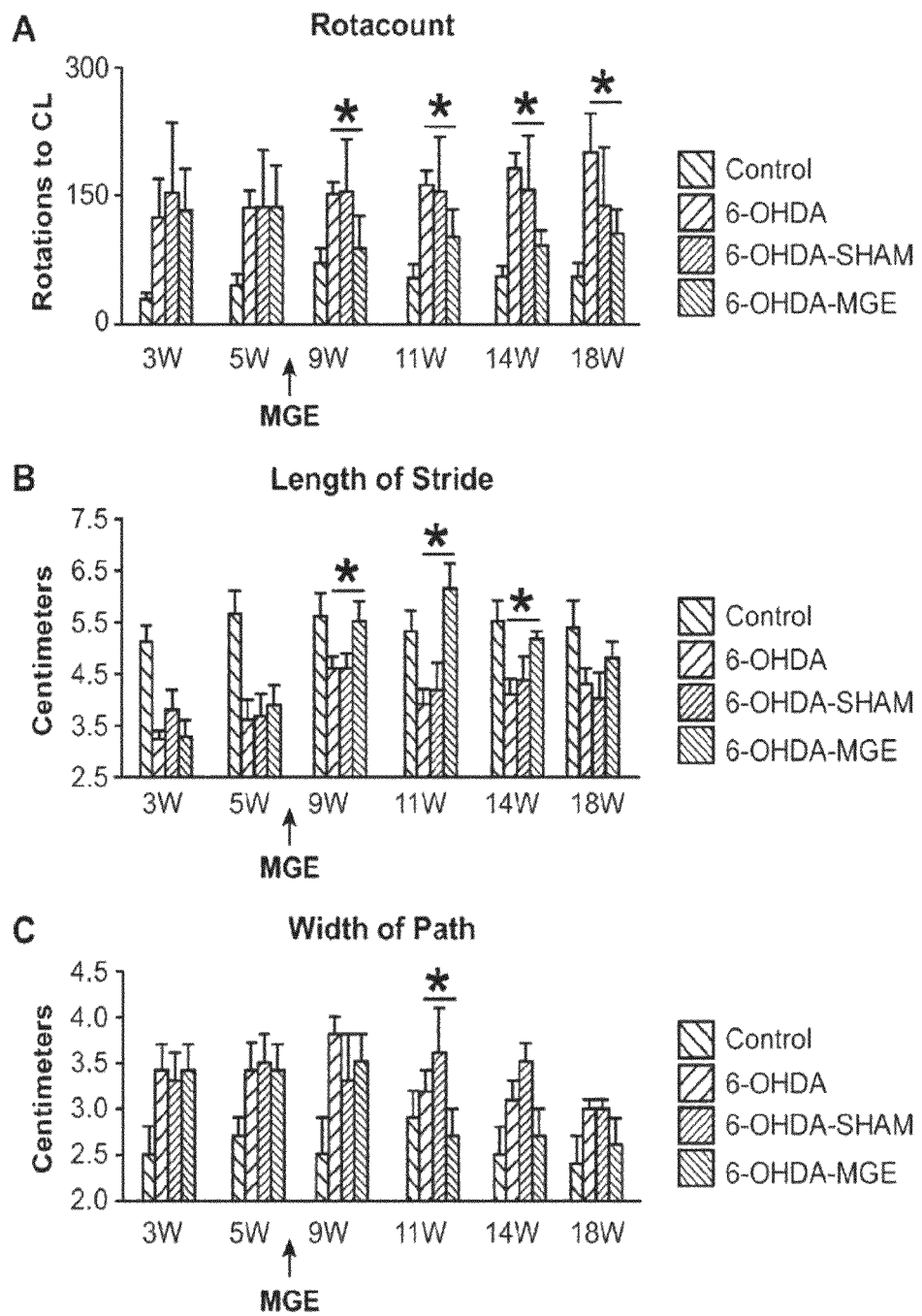
FIG. 5 is a collection of graphs as follows: Panel A. Rotation test. 6-OHDA rats (n=21) performed far more rotations than control rats (n=16) before receiving an MGE cell transplant. Upon transplantation, however, they started performing significantly fewer contra-lateral turns than non-transplanted 6-OHDA controls (n=12). This trend continued until the last time point (week 18). Sham-transplanted 6-OHDA rats (n=11) performed similarly to non-transplanted 6-OHDA rats (n=12). Panel B. Length of stride test. 6-OHDA rats (n=12) had an average stride length of 13.2±0.2 cm, significantly shorter than the average stride length of control rats (15.1±0.3, n=16). Upon MGE cells transplantation, the stride length of 6-OHDA rats increased and eventually reached the same value as in control rats (15.5±0.4 cm, n=21). The stride length of 6-OHDA rats that had received a sham transplant (n=11) was not significantly different from that of 6-OHDA rats (n=12). Panel C. Width of path test. 6-OHDA rats had a width of path of 3.4±0.3 cm (n=12), significantly different from the 2.5±0.3 cm width of path of control rats (n=16). Upon MGE cells transplantation, the path width decreased and eventually reached control value (n=16). The path width of sham transplanted 6-OHDA rats (n=11) was not significantly different from that of 6-OHDA rats (n=12).

MGE Cell Striatal Grafts Ameliorated the Behavioral Symptoms of 6-OHDA Lesioned Rats The behavioral effect of MGE cells on 6-OHDA lesioned rats was examined using three behavioral tests performed before and after transplantation (FIG. 5).

Rotation under apomorphine As previously shown, upon apomorphine administration, unilaterally 6-OHDA lesioned rats rotated significantly more to the contralateral side (with respect to the lesioned side) than the ipsilateral side compared to control rats that rotated approximately equally in both directions. After transplantation, there was a significant reduction in the number of contra-lateral turns in the MGE transplanted 6-OHDA lesioned rats (n=21) compared to non-transplanted 6-OHDA controls (n=12). This effect was observed at all experimental times beginning with week 9 ($p<0.05$) and continued until the last time point, 18 weeks ($p<0.05$). The performance of sham-transplanted 6-OHDA rats (n=11) was undistinguishable from non-transplanted 6-OHDA rats (n=12), indicating that the MGE cells, and not the transplantation procedure, were responsible for the motor improvement of MGE-transplanted 6-OHDA rats. (FIG. 5, Panel a).

Figure 6:
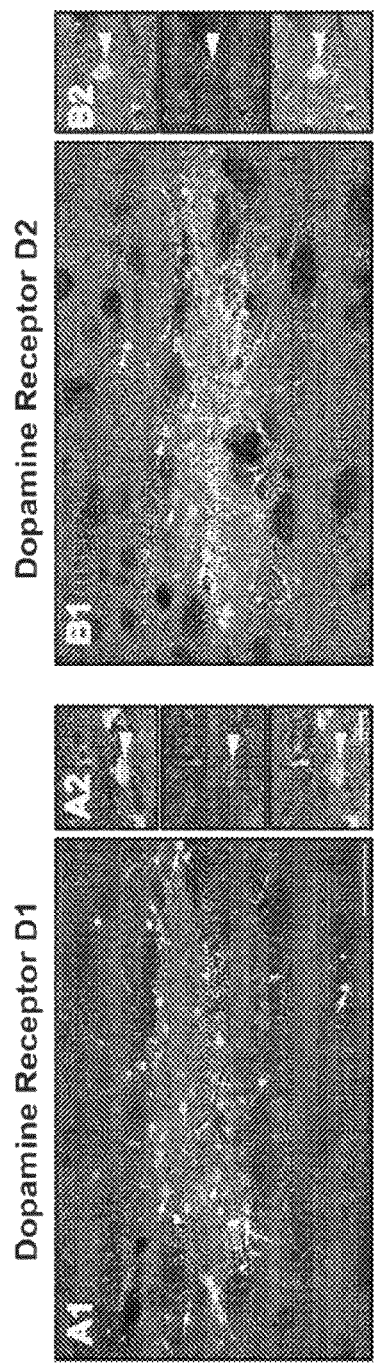
FIG. 6 is a collection of images showing MGE transplanted cells expressed Dopamine Receptors 1 (DR1, A1-A2) and Dopamine Receptor 2 (DR2, B1-B2). DR1 and DR2 are present in somatic membrane and processes of MGE cells. Panels A2 and A3. High magnification images of MGE cells that expressed DR1 (A2) and DR2 (B2). Panel A1=30 µm and applies to Panel B1; Panel A2=3 µm and applies to Panel B2.

Apomorphine binds to dopamine receptors expressed by host striatal neurons, which causes rotation in the 6-OHDA rat (Ungerstedt and Arbuthnott, 1970). Apomorphine-induced rotational behavior was significantly reduced after MGE transplantation suggesting that the transplanted MGE cells express dopamine receptors and are directly responsible for the observed reduction in rotational behavior. This hypothesis was confirmed by performing fluorescence immunostaining for dopamine receptor 1 (DR1) and 2 (DR2). Both were detected in somatic membrane and processes of MGE cells 12 weeks after transplantation (FIG. 6). These data demonstrate that apomorphine directly stimulates MGE inhibitory interneurons, altering the balance of excitation/inhibition in the striatum and modifying rotational behavior.

Length of stride 6-OHDA rats (n=12) had a stride length of 13.2±0.2 cm, significantly shorter than the stride length of control rats, 15.1±0.3 cm ($p<0.001$, n=16). After MGE cell transplantation, the stride length of the 6-OHDA rats (n=21) increased and by week 9 reached values similar to those of control rats (15.5±0.4 cm, n=16). The increase in the length of stride was maintained after 11 and 14 weeks. The stride length of 6-OHDA rats that received a sham transplant (n=11) did not change, and was not significantly different from that of 6-OHDA rats that received no treatment (n=12) (FIG. 5, Panel b).

Width of path The maximum path width of all rats was measured as they ran down the runway (FIG. 1, Panel e). 6-OHDA animals (n=12) had a path width that was 3.4±0.3 cm, which was significantly wider than the value of 2.5±0.3 cm for control rats ($p<0.05$, n=16). The path width of 6-OHDA rats that received MGE cell transplants decreased and by week 11 matched (2.7±0.3 cm, n=21) that of the unlesioned control animals (n=16). The path of sham transplanted 6-OHDA rats (n=11) was not significantly different from that of 6-OHDA rats (n=12). These data indicate that MGE transplantation resulted in a substantial improvement in the gait of 6-OHDA lesioned rats (FIG. 5, Panel c).

MGE Cell Striatal Transplants Alter the Motor Performance of Wild-Type Rats

Figure 7:
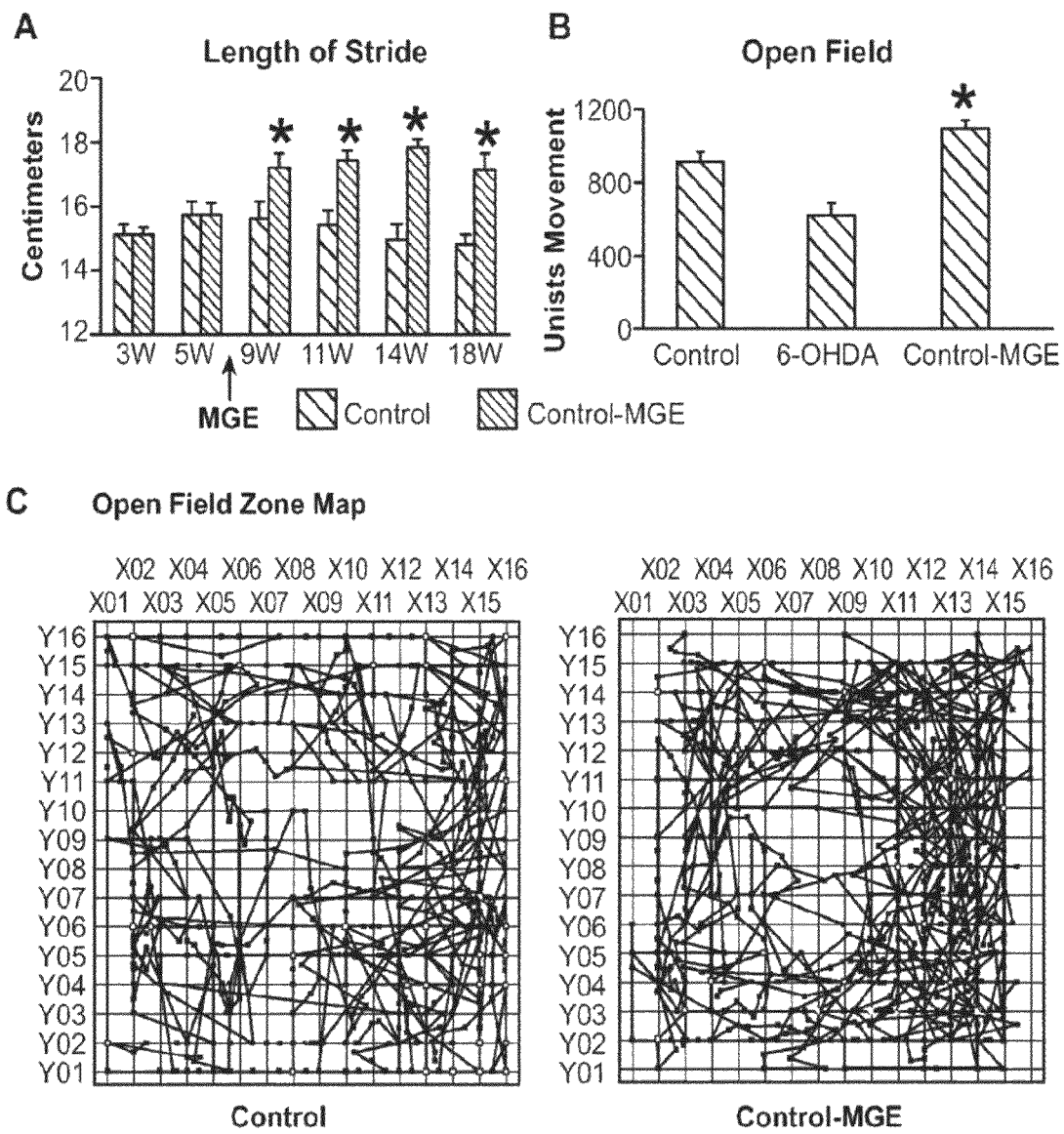
FIG. 7 is a collection of graphs showing the following: Panel A. The length of stride was significantly higher in control rats injected with MGE cells (n=6) than in control rats (n=16). Panel B. Open field test show an increase activity in wild-type MGE transplanted rats compared to control rats. Panel C. Representative open field zone map. Wild-type MGE transplanted rat has a major level of motor activity when compared to a control rat.

MGE cells were grafted into intact rats to examine the effect of MGE cells on unlesioned animals using the behavior assays described above. The path width and the rotations under apomorphine were not significantly different in rats injected with MGE cells compared to non-transplanted controls. Interestingly, the stride length of wild-type rats that received MGE grafts was significantly longer than that of control untreated rats ($p<0.001$, n=6) (FIG. 7, Panel a). This was believed due to an increase in motor activity after MGE-transplantation. To confirm this hypothesis an open field activity test was performed on wild-type control, 6-OHDA injected and MGE-transplanted wild-type rats using a five minute test period (FIG. 7, Panel b). Surprisingly, MGE-cells transplanted into control rats (no 6-OHDA treatment) produced a significantly higher level of motor activity (1101±39 UM) than in untreated control rats (912±104 UM). 6-OHDA injected rats, as expected, had lower motor activity levels than control rats (453±69 UM). The increase of motor activity in wild-type rats versus control rats is reflected in the open field zone map (FIG. 7, Panel c).

Figure 8:
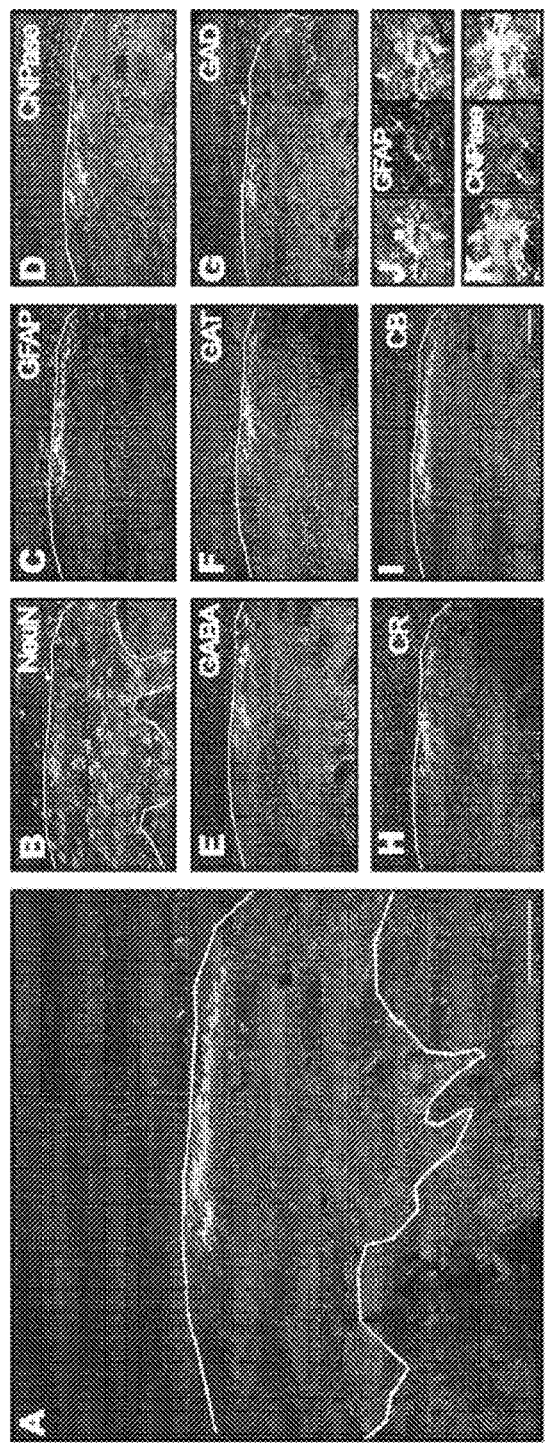
FIG. 8 is a collection of images showing MGE cells transplanted into the STN survived but did not migrate from the site of injection (Panel A). None of the MGE cells in the STN expressed the neuronal marker NeuN (Panel B), the inhibitory interneuron markers GABA (Panel E) or GAD (Panel G), or the calcium sequestering proteins CR (Panel H) or CB (Panel I). MGE cells transplanted STN expressed GFAP (75±5%, Panels C and J) or the oligodendrocyte marker CNPase (30±9%, Panels D and K). A small percentage of MGE cells in the STN expressed the GABA transporter GAT1 (13±5%, Panel F). Scale bars: A=25 µm; I=25 µm and applies to Panels B, C, D, E, F, G and H; K=5 µm and applies to J.

MGE Cells Transplanted in the Subthalamic Nucleus Survived, but Did not Migrate, and Transformed into Glial Cells The results observed after MGE cell transplantation into the striatum suggests that increased GABAergic inhibition in the striatum significantly ameliorates motor symptoms in hemi-Parkinsonian rats. It has been suggested that increasing inhibition in the subthalamic nucleus (STN) could also have beneficial effects in Parkinson's disease (Benabid et al., 2000; During et al., 2001). Therefore, the survival and differentiation of grafted MGE cells were tested in this nucleus. The behavior and phenotype of MGE cells, however, was strikingly different after transplant into the STN. In contrast to MGE cells that migrated substantial distances after transplant into the striatum, MGE cells transplanted into the STN did not migrate from the site of injection (n=6, FIG. 8, Panel A). Moreover, the MGE cells in the STN did not become neurons. None of the MGE cells in the STN expressed the neuronal marker NeuN (n=231). In contrast, a small number of MGE cells located outside the boundary of the STN did express NeuN (FIG. 8, Panel B). Furthermore, none of the grafted MGE cells in the STN expressed the calcium sequestering proteins CR or CB, or the inhibitory interneuron markers GAD or GABA (FIG. 8, Panels E, G, H, I). While none of grafted MGE cells in the striatum expressed the astrocyte marker GFAP, the majority of MGE cells in the STN expressed GFAP (75±5%, n=151). Roughly one third of MGE cells also expressed the oligodendrocyte marker CNPase (30±9%, n=132, FIG. 8, Panels C,D,J,K) A small percentage of MGE cells in the STN expressed the GABA transporter GAT1 (13±5%, n=94, FIG. 8, Panel F). The GAT expressing cells were most likely astrocytes or oligodendrocytes which have been shown to express the GAT1 GABA transporter (Pow et al., 2005). These data indicate that, in contrast to the striatum where MGE grafted cells integrate and differentiate into neurons, most grafted MGE cells in STN differentiate into glial cells.

Example 2

In this study, MGE cell transplantation was tested as a means to add inhibitory GABAergic interneurons to the striatum. Additionally, MGE cell transplantation was tested to see if it would beneficially improve the motor behavior of hemi-Parkinsonian rats. These studies utilized MGE cells from E14.5 GFP rats that were transplanted into the striatum of adult rats. A small population of these transplanted cells, migrated, survived and differentiated into GABAergic neurons that became synaptically integrated into the striatal circuitry. MGE cells that were grafted into the striatum of 6-OHDA lesioned rats alleviated motor symptoms of PD. Fetal MGE grafts in the striatum also impacted the behavior of normal untreated rats; the transplanted MGE cells increased several measures of motor activity in the control animals. The ability of MGE cells to differentiate into interneurons appears to be dependent on the host environment since transplanted MGE cells into the STN differentiated into astrocytes or oligodendrocytes rather than neurons. These data indicate that injection of MGE cells into the striatum is a new modality to modulate hyperactive neurons in the striatum and therefore alleviate motor symptoms in PD.

MGE Cells Transplanted into the Adult Striatum Transform into Inhibitory Interneurons and Integrate into the Striatal Circuit MGE cells transplanted into the striatum survived at least one year, migrated from the site of injection, and were widely distributed throughout the striatum. This study demonstrated that MGE cells transplanted into the adult striatum acquire a mature morphological phenotype and differentiate into GABAergic neurons that express markers common to neostriatal interneurons. Although a small percentage of the MGE transplanted cells survived after 3 months, the ability of these cells to impact behavior depends on their number in relation to the number of host interneurons. Stereological based studies estimate that the number of striatal interneurons in the adult rat is approximately 49,000: 13,000 CR+ interneurons (Rymar et al., 2004), 15,000 PV+ interneurons (Larsson et al., 2001; Luk and Sadikot, 2001) and 21,000 SOM+ interneurons (West et al., 1996). Therefore, the average number of transplanted MGE cells that survived in the current experiments (2613±156, n=3) represents approximately 5% of the total number of native striatal interneurons. In addition, the MGE cells extended numerous processes throughout the striatum, indicating their potential for interacting widely with host cells. The number of surviving MGE cells are sufficient to produce motor behavioral changes, both in 6-OHDA treated, and untreated control animals. MGE cells unexpected demonstrated the generally effect of increasing motor speed of all treated animals, including the unlesioned, control animals. The transplantation of a higher number of MGE cells is anticipated to result in a greater number of surviving interneurons in the host striatum.

The embryonic MGE produces both striatal and neocortical interneurons, and both populations share the expression of many of the same sets of markers (Defelipe et al., 1999; Kawaguchi, 1997; Kubota et al., 1994). Thus, it is likely that the dissociated embryonic MGE cells that were injected into the striatum included a mixture of cells destined to populate both the striatum and the neocortex, and these cells retained their normal molecular expression characteristics after transplantation. However, the pattern of cell markers expressed by MGE cells was influenced by their post transplantation environment as most MGE cells that survived in the adult STN nucleus expressed GFAP and none expressed neuronal markers.

GFP+ processes were not detected outside of the striatum in the transplanted animals, indicating that the transplanted MGE cells did not project outside of the striatum as do GABAergic projection neurons. Thus, the MGE cells integrated in the circuitry of the striatum and the behavioral changes observed in transplanted rats were due to modification of activity of synapses and/or neurons within the striatum by the transplanted cells. This integration modulated the activity level of host GABAergic interneurons and/or projection neurons and produced a remarkable improvement in the behavioral deficits.

Transplanted MGE Cells Ameliorate Behavioral and Movement Deficits in 6-OHDA Rats 6-OHDA lesioned rats that received MGE cell grafts exhibited behavioral improvements including improvement in the apomorphine rotational test, an increase on the length of stride, and a normalized gait. These behavioral and movement changes indicate a general improvement of the motor symptoms of PD animals after MGE transplantation.

MGE cells were transplanted six weeks after the induction of 6-OHDA lesions. The MGE cells differentiated into GABA+ interneurons within 4 weeks after transplant and notably improved motor symptoms of PD. These results demonstrate that, in addition to the protective effect described previously, GABA also improve PD symptoms once the disease is established. The ability of MGE cells to disperse in the striatum, mature, remain functionally active, and synaptically integrate into basal ganglia circuitry is responsible for the observed behavioral modifications. MGE cells can also carry trophic factors or neurotransmitter synthesizing enzymes to further ameliorate symptoms produced by dysfunctional circuits in the striatum. Useful neurotrophic factors include the neurotrophins (e.g., NGF; brain-derived neurotrophic factor, BDNF; and neurotrophins NT-3 and NT-4/5); the neuropoietic cytokines (e.g., ciliary neurotrophic factor, CNTF); and the fibroblast growth factors (e.g., acidic and basic FGF). Useful neurotransmitters include acetylcholine, epinephrine, norepinephrine, dopamine, serotonin, melatonin, glutamic acid, gamma aminobutyric acid (GABA), aspartic acid, and glycine.

The increase in motor behavior observed after transplantation of fetal MGE cells into the striatum of control rats, indicates that MGE cells are ideal for achieving a change in the balance of excitatory and inhibitory signals in the striatum, and thus represent a powerful strategy for altering output of the striatum in disease conditions.

Therapeutic Advantages

The approach of the methods of the present disclosure is to inject dissociated cells from the embryonic MGE into the adult basal ganglia of a subject having or suspected of having PD, epilepsy or other neurological condition amenable to treatment according to the methods disclosed herein. The advantage of MGE cell transplants over other cell types is their capacity for dispersal throughout the striatum. For example, mesencephalic cells show very little migration after transplantation into the striatum and remain in clumps within the basal ganglia. These clusters are thought to be responsible for some of the serious side effects that result from transplantation of dopaminergic precursors for PD (Bhattacharya et al., 2004). In contrast, the MGE cells have the surprising ability to disperse widely after transplantation and integrate into the host striatum in a homogenous manner that lessens PD symptoms without undesired side effects seen in other therapies. MGE grafts do not produce tumors or cause aberrant tissue organization. Striatum grafted MGE cells increase motor activity levels, demonstrating that MGE cells change the balance of excitatory and inhibitory activity. In some embodiments, MGE grafts reduce one or more TRAP features of PD and/or reduce flexed posture and freezing by at least 10% compared to controls or the previous untreated state. In some embodiments, MGE grafts reduce one or more TRAP features of PD and/or reduce flexed posture and freezing by at least 20%, 30%, 40%, 50%, 60%, 70%, 80%, 90%, or 95% compared to controls or the previous untreated state. In some embodiments, MGE grafts reduce the amount of required drug by at least 10% compared to controls or the previously untreated state. In some embodiments, MGE grafts reduce the amount of required drug by at least 20%, 30%, 40%, 50%, 60%, 70%, 80%, 90%, or 95% compared to controls or the previously untreated state. In some embodiments, MGE cells transplanted into the striatum survive for at least 6 months. In some embodiments, MGE cells transplanted into the striatum survive for at least 1, 2, 3, 4, 5, 7, or 10 years. In some embodiments, treatment of patients suffering from bradykinesia is preferred. In some embodiments, before and after treatment success is measure under at least one of the following criteria, the unified Parkinson's disease rating scale (UPDRS), motor "off" (off medication) scores, OFF time and dyskinesias, and dose of L-Dopa.

Example 3 Epilepsy

Figure 9:
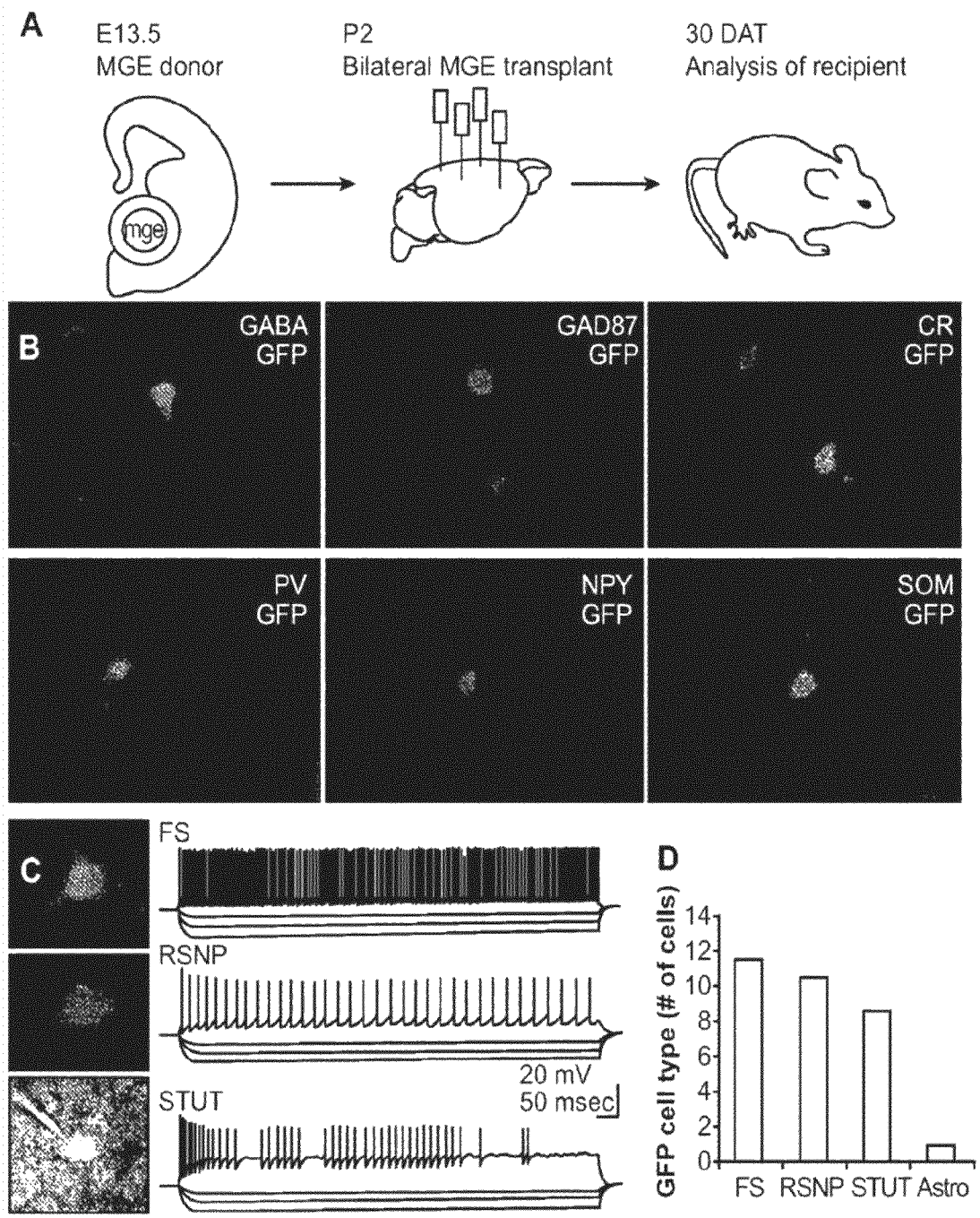
FIG. 9 is a collection of schematics and images showing the following: Panel A generally illustrates the transplantation of MGE cells from E13.5 embryonic GFP+ transgenic donor into mice expressing green fluorescent protein (GFP) on postnatal day 2 (P2); bilateral injections were made. MGE cells are then analyzed 30 days after transplantation (30 DAT). Panel B illustrates transplanted MGE cells, harvested from mice expressing GFP at 30 DAT and co-labeled with antibodies to GABA, GAD67, calretinin (CR), parvalbumin (PV), neuropeptide Y (NPY), and somatostatin (SOM). Panels C and D illustrate that the MGE-GFP neurons exhibit firing properties similar to endogenous interneuron sub-types such as fast-spiking (FS), regular-spiking non-pyramidal cells (RSNP), and stuttering (STUT). The plot in 1d summarizes all GFP-positive cells that were recorded; one cell had non-firing properties similar to an astrocyte (astro).

Transplanted MGE cells, harvested from mice expressing green fluorescent protein (GFP), co-label with antibodies to GABA, GAD67, calretinin, parvalbumin, neuropeptide Y or somatostatin at 30 days after transplantation (30 DAT) (FIG. 9, Panels A, B). In neocortical tissue slices from 30 DAT grafted animals, MGE-GFP neurons primarily exhibit firing properties similar to endogenous interneuron sub-types: (i) fast-spiking, (ii) regular-spiking non-pyramidal cells and (iii) burst-spiking non-pyramidal (FIG. 9, Panels C-D). Consistent with previous observations of graft-derived cells with immature and "migratory" anatomical profiles immediately following transplantation (Wichterle 1999; Alvarez-Dolado 2006), current-clamp recordings at 7 to 10 DAT revealed GFP+ neurons with immature intrinsic membrane properties e.g., small and broad width action potentials, depolarizing resting membrane potential and high input resistance (data not shown). As expected at 30 DAT (Alvarez-Dolado 2006), GAB A-mediated input to pyramidal neurons in the host brain, measured as inhibitory postsynaptic current (IPSC) frequency, increased by nearly 300% in mice receiving MGE grafts (control: 0.6±0.1 Hz, n=8; MGE: 2.3±0.3 Hz, n=7).

Figure 10:
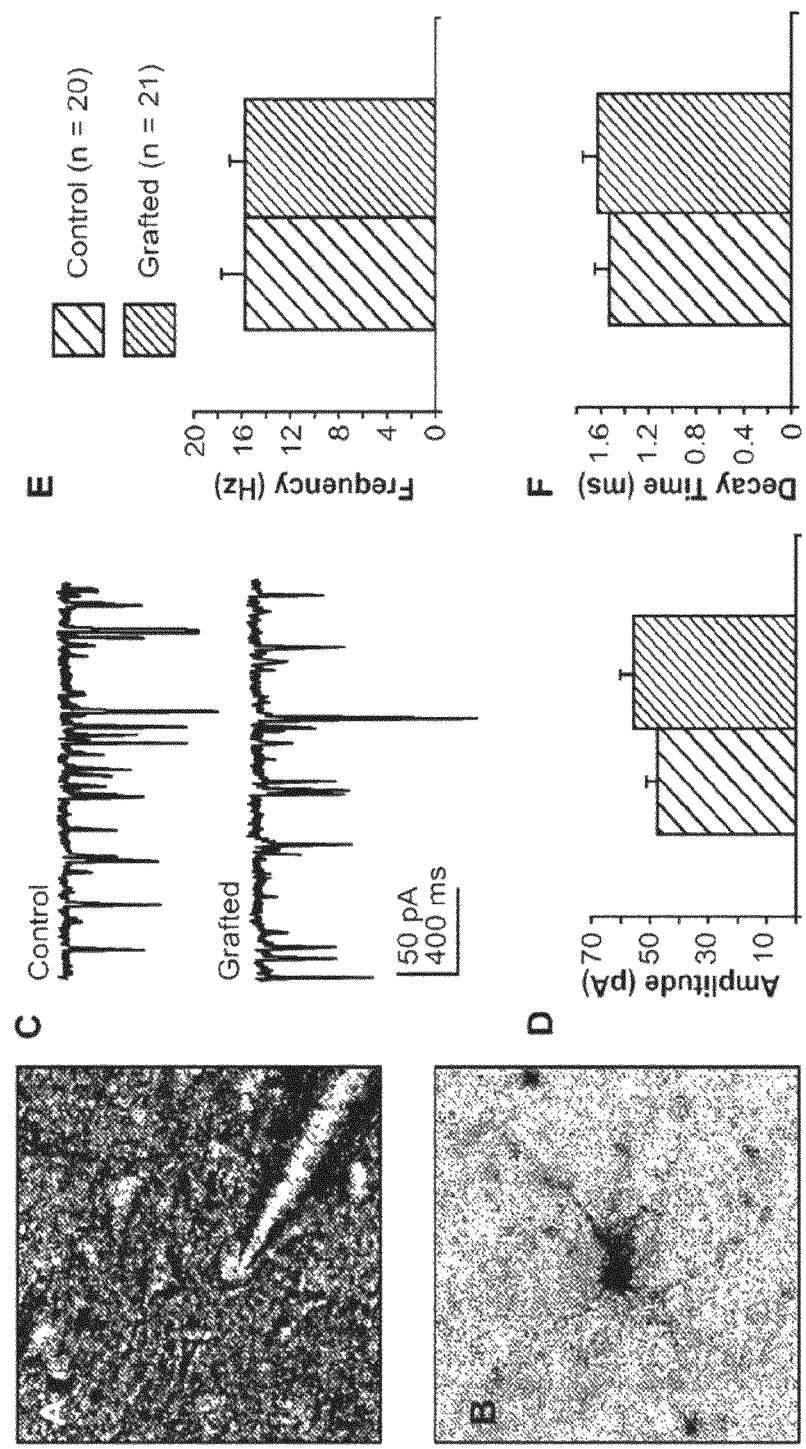
FIG. 10 is a collection of graphs and images as follows: Panel A shows an interneuron, identified by their oval and often multi-polar morphologies under IR-DIC. Panel B confirms post hoc that the interneurons were correctly identified with biocytin labeling. Panel C shows GABA-mediated current from control (un-transplanted) and grafted interneurons that were voltage-clamped in bath solution containing glutamate receptor antagonists (DNQX and APV). Panels D-F show no significant differences in GABA-mediated inhibition onto endogenous interneurons between control and grafted mice at 30 DAT using IPSC analysis.

MGE progenitors were examined for their ability to generate interneurons that would innervate native interneurons and alter the activity of the endogenous interneurons, an undesirable side effect. To determine whether GABA-mediated inhibition onto endogenous interneurons was altered, the spontaneous IPSCs in the host neocortex of grafted mice were examined. Interneurons were identified by their oval, often multi-polar morphologies under IR-DIC (FIG. 10, Panel a), confirmed post hoc with biocytin labeling (FIG. 10, Panel b) and voltage-clamped in bath solution containing glutamate receptor antagonists (DNQX and APV; FIG. 10, Panel C) to isolate GABA-mediated current. IPSC analysis failed to identify significant differences between control (un-transplanted) and grafted mice at 30 DAT (FIG. 10, Panels d-f).

Figure 11:
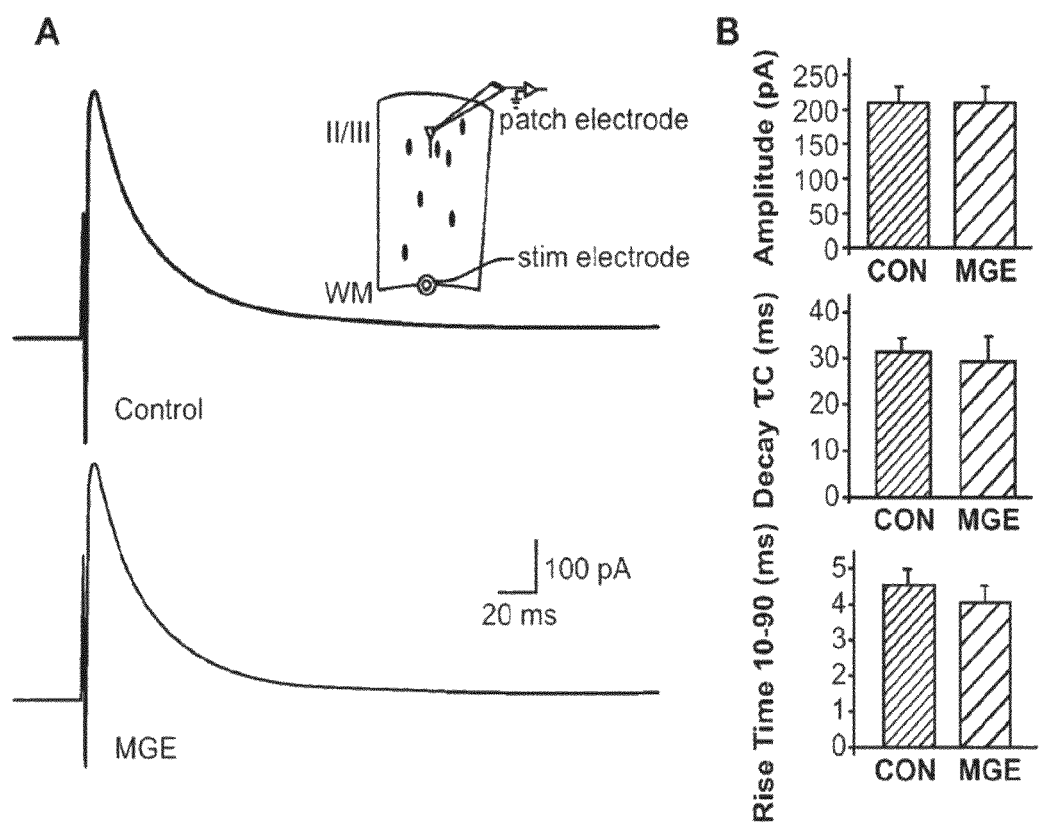
FIG. 11 shows that white matter stimulation elicited IPSCs on Layer II/III pyramidal neurons in regions containing GFP+ cells with kinetic properties that were not different between control and grafted animals.

Enhanced inhibition in grafted animals could also lead to homeostatic changes in postsynaptic GABAA receptors (Mody 2005; Xu 2007). Analysis of evoked IPSC kinetics, decay time constants in particular (Soltesz; MV Jones), would reflect potential changes in postsynaptic GABA receptor subunit expression and were examined in neocortical slices (30 DAT). White matter stimulation elicited IPSCs on Layer ii/III pyramidal neurons in regions containing GFP+ cells with kinetic properties that were not different between control and grafted animals (FIG. 11). Together, these data further support the MGE transplantation protocol as an effective strategy to selectively enhance inhibition of principal neurons in postnatal brain.

Figure 12:
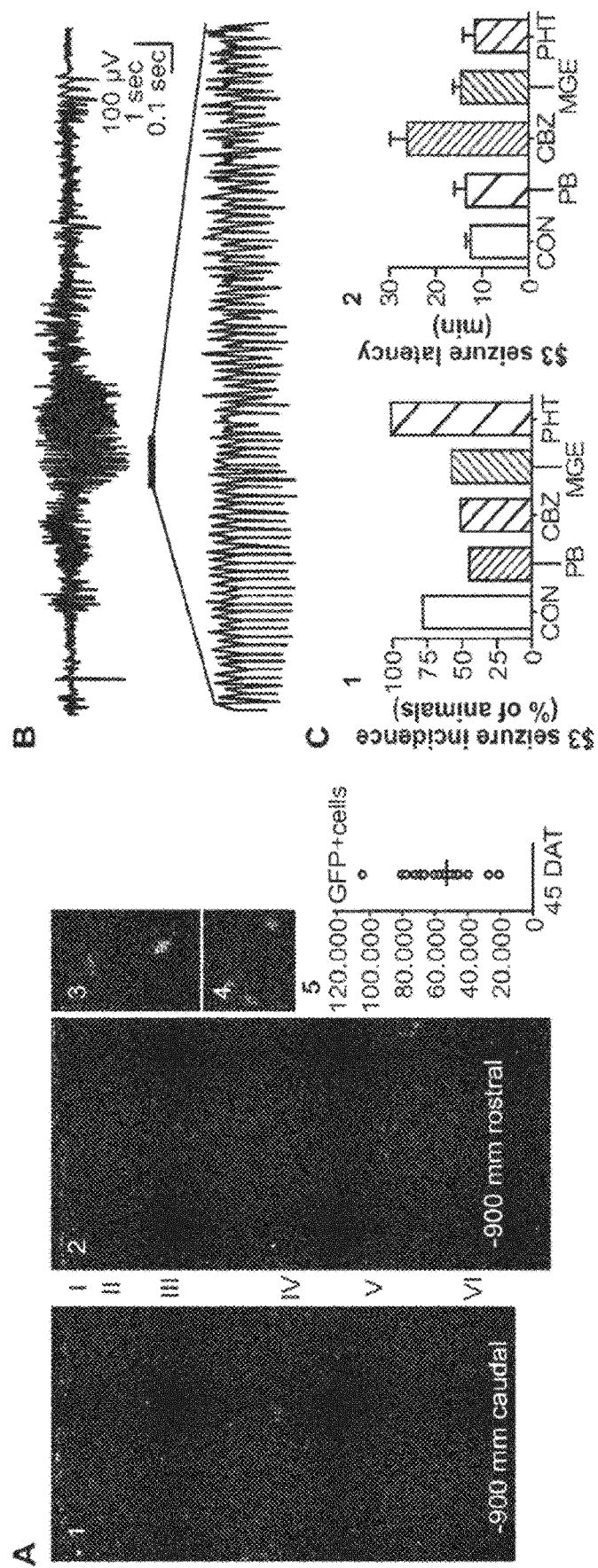
FIG. 12 is a collection of images and graphs as follows: Panel A, subpanels 1-4 show that early postnatal bilateral transplantation of MGE-GFP progenitors generated new GFP-immunoreactive (IR) cells in host neocortex with distributions between 0.75 and 5 mm from injection site. Panel A, subpanel 5 show that a threshold of ~40,000 GFP-IR cells per animal, with migration ≥0.5 mm from the injection site, was defined as a successful graft. Panel B illustrates confirmation of high-amplitude synchronous electrographic seizure activity using scalp electroencephalographic (EEG)

Because some available antiepileptic drugs (AEDs) enhance GABA-mediated synaptic transmission and enhanced inhibition could be therapeutic (MacDonald 1989), MGE transplants were examined for their ability to reduce acute seizures. Early postnatal bilateral transplantation of MGE-GFP progenitors generated new GFP-immunoreactive (IR) cells in host neocortex with distributions between 0.75 and 5 mm from the injection site (FIG. 12, Panels a1-4; also see Alvarez-Dolado 2006). New interneuron density was confirmed for all animals used in acute seizure studies and a threshold of approximately 40,000 GFP-IR cells per animal, with migration ≥0.5 mm from the injection site, was defined as a successful graft (FIG. 12, Panel a5). Pilocarpine, a muscarinic acetylcholine receptor antagonist and common convulsant agent, was administered to adult wild-type mice at a concentration (300 mg/kg, i.p.) chosen to maximize the number of animals that would experience tonic-clonic seizures (Winawer et al. 2007). High-amplitude synchronous electrographic seizure activity was confirmed using scalp electroencephalographic (EEG) recording and dual digital cameras (FIG. 12, Panel B). Behavioral seizure manifestations including forelimb clonus (Stage III, S3; Racine 1972; Jones 2002) were observed in ~75% of control mice at this pilocarpine concentration; the latency to first behavioral seizure was between 10 and 15 minutes post-injection, as reported previously (Hamani 2004). In mice grafted with MGE cells at P2, the percentage of animals exhibiting S3 seizures was reduced to approximately 50% (FIG. 12, Panel c1); latency to first seizure behavior was unchanged (FIG. 12, Panel c2). This level of "seizure protection" was comparable to that observed with phenobarbital (20 mg/kg) or carbamazepine (50 mg/kg) pre-treatment, and better than phenytoin (200 mg/kg), an AED previously shown to exacerbate pilocarpine-induced seizures (Sofia et al., 2003)(FIG. 12, Panel d2).

MGE transplants were then tested for their ability to reduce seizures in a mouse epilepsy model. Spontaneous tonic-clonic seizures were reported in humans with a dominant-negative missense mutation in KCNA1 (Zuberi 1999) or mice with a recessive knockout of Kv1.1/Kcna1 (Smart 1999). To monitor spontaneous seizures in these mice, prolonged video-electroencephalography (EEG; see Methods for full description of electrographic phenotypes) was performed. The EEG of Kv1.1-1-mice showed severe, generalized electrographic seizures lasting 10-340 s (Grade IV; FIG. 13, Panel A) and occurring more than once per hour (1.5±0.5 seizure/hr; FIG. 13, Panel C); electrographic seizures or high voltage spiking were never observed in age-matched wild-type siblings (FIG. 13, Panel A). Video monitoring confirmed tonic-clonic, S4 seizure behavior (e.g., tonic arching, tail extension, followed by forelimb clonus, and then synchronous forelimb and hindlimb clonus) during ictal seizure episodes. As reported (Smart 1999; Wenzel 2007; Glasscock 2007), Kv1.1-1-mice exhibit frequent spontaneous seizures starting during the second-to-third postnatal week and do not survive beyond the 8th postnatal week (FIG. 13, Panels a-e); sudden death is likely due to cardio-respiratory failure associated with status epilepticus. In contrast, Kv1.1-1-mice grafted with MGE progenitors on P2 survive well past postnatal week 10 and exhibit a surprising and striking reduction in electrographic seizure activity. Only brief episodes (10-48 s) of synchronized high amplitude spiking were observed in transplanted Kv1.1-1-mice (FIG. 13, Panels a, b). The frequency of these events was rare compared to un-transplanted mice (FIG. 13, Panel c) and 43% of grafted animals only exhibit interictal spiking (Grade II; Table 1). Kaplan-Maier survival plots show a clear, and statistically significant, rightward shift for Kv1.1 mutant mice receiving successful MGE grafts (FIG. 13, Panel d); new GFP cell density was confirmed as 40,000 cells per brain in Kv1.1-1-mice that survived to P57 (FIG. 13, Panels e-f).

Embryonic neural progenitor cells derived from the medial ganglionic eminence generate new interneurons. These cells differentiate into functional interneuron subtypes and selectively enhance GABA-mediated inhibition in the host brain. Newly-generated interneurons demonstrate a surprising protective effect against acute seizures that was comparable to that observed with commercially available AEDs. In some embodiments, MGE progenitor cell transplantation results in a reduction of required AED dose of at least 10% compared to untreated controls or to the individual's previously untreated state. In some embodiments, MGE progenitor cell transplantation results in a reduction of required AED dose of at least 20%, 30%, 40%, 50%, 60%, 70%, 80%, 95%, or 99%, compared to untreated controls or to the individual's previously untreated state. Significant suppression of spontaneous seizures was observed in a mouse model of generalized epilepsy. Decreased seizure activity in these animals was also associated with a delay in sudden death and significantly prolonged life-span.

Immortalized cells engineered to produce GABA attenuate stimulation-induced electrical afterdischarge in a rat (Thompson 2000; 2005). Attenuation of afterdischarge duration has also been achieved with embryonic precursor cells modified to release adenosine (Li 2007) or viral vectors engineered to produce glial-cell line-derived neurotrophic factor (Kanter-Schlifke 2007), neuropeptide Y (Richichi 2004) or galanin (Haberman 2003; McCown 2006). While promising, none of these procedures was associated with migration (or transfection) of cells outside the injection site, functional evidence for modification of synaptic transmission in the host brain or significant suppression of spontaneous electrographic seizures. Systemically injected human neural stem cells modestly reduce behavioral seizures in a rat pilocarpine model and hippocampal field recordings suggest an effect on synaptic inhibition (Chu 2004). These studies, and the demonstrated differentiation of hippocampal neural stem cells into neurons (including GABAergic interneurons) in a rat model of temporal lobe epilepsy (Shetty, 2005), suggest that interneuron generation and enhancement of GABAergic neurotransmission (as shown here in single-cell recordings) may be antiepileptic. Although interneuron loss has been reported in epilepsy (de Lanerolle 1989; Spreafico 1998; Golarai 2001), and GABA-enhancing AEDs are used clinically (MacDonald 1986, 1989), a procedure to modify host brain circuits via the addition of new interneurons to existing circuits, either normal or pathological, has never been demonstrated.

MGE cell grafts were shown to produce a dramatic and remarkable reduction in spontaneous electrographic seizure activity in a mouse Shaker-like K+ channel mutant mimicking a human epilepsy phenotype (Kuberi; Noebels). In some embodiments, at least a 10% reduction in spontaneous electrographic seizure activity is achieved. In some embodiments, at least a 20%, 30%, 40%, 50%, 60%, 70%, 80%, 95%, or 99% reduction in spontaneous electrographic seizure activity is achieved. In some embodiments, at least a 10% reduction in the duration of seizures is achieved. In some embodiments, at least a 20%, 30%, 40%, 50%, 60%, 70%, 80%, 95%, or 99% reduction in the duration of seizures is achieved. In some embodiments, at least a 10% reduction in the frequency of spontaneous electrographic seizures is achieved. In some embodiments, at least a 20%, 30%, 40%, 50%, 60%, 70%, 80%, 95%, or 99% reduction in the frequency of spontaneous electrographic seizures is achieved. In some embodiments, at least a 10% reduction in high voltage spiking is achieved. In some embodiments, at least a 20%, 30%, 40%, 50%, 60%, 70%, 80%, 95%, or 99% reduction in high voltage spiking is achieved. This result is consistent with a long-standing hypothesis that synaptic inhibition constrains seizure discharge (Kandel, Dichter, Trevelyan). Moreover, the described transplantation protocol to generate enriched populations of GABAergic interneurons with the unique ability to migrate and functionally integrate in host brain provides a significant advancement in cell therapy development for the treatment of intractable epilepsy.

Methods

Tissue dissection and cell dissociation. Ventricular and subventricular layers of the GE germinal region were dissected from E13.5 embryonic GFP+ transgenic mice. The MGE is a transient structure, and at E14 the MGE is well developed but still separated from LGE. Bordering tissue between adjacent regions was discarded during dissections to avoid contamination. Explants were mechanically dissociated by repeated pipetting through 200 µl yellow plastic pipette tip (10-20 times). Dissociated cells were washed with 1 ml of L-15 medium containing DNase 1 (10-100 µg/ml) and pelleted by centrifugation (2 minutes, 800 g).

Transplantation. Highly concentrated cell suspension (~8×105 cells/µl in 3-5 µl of L-15 medium) were front-loaded into beveled glass micropipettes (~50 µm diameter) that pre-filled with mineral oil and mounted on a microinjector. Cells were allowed to settle inside the pipette and the excess cell-free medium will be expelled. Two-three day old mice were anesthetized by exposure to −4° C. until pedal reflex was abolished. Anesthesia was maintained by performing surgery on a cold aluminum plate. 5×105 cells/mouse were injected in deep layers of cortex.

Immunostaining. Animals were transcardially perfused with 4% paraformaldehyde. Brains were immediately removed, postfixed overnight, and sectioned coronally (50 µm). Floating sections were immunostained with commercially available antibodies. Secondary antibodies were used: cy3-conjugated donkey anti-mouse, cy3-conjugated donkey anti-rabbit, cy2-conjugated donkey anti-rabbit, and biotin-conjugated donkey anti-mouse (all from Jackson ImmunoResearch, PA). Sections were washed in PBS, blocked for 1 h in PBS containing 10% donkey serum and 0.1% Triton X-100, then incubated overnight at −4° C. in primary antibodies diluted in PBS containing 10% donkey serum and 0.1% Triton X-100, washed 3× in PBS and incubated with secondary antibodies for 1-2 hours at room temperature in the dark. Fluorescent images were obtained using a cooled-CCD camera (Princeton Instruments) and Metamorph software (Universal Imaging).

Electrophysiology. Acute neocortical slices were prepared from male or female mice, as described previously (Alvarez-Dolado et al. 2005). Resulting slices were immediately transferred to a holding chamber where they remained submerged in oxygenated recording medium (ACSF) consisting of (in mM) 124 NaCl, 3 KCl, 1.25 $NaH_2PO_4$, 2 $MgO_4$, 26 $NaHCO_3$, 2 $CaCl_2$, 10 dextrose (295-305 mOsm); 37° C. for 45 min and then at room temperature. For each experiment an individual slice is gently transferred to a recording chamber and continuously perfused with oxygenated recording medium at room temperature. Whole cell voltage-clamp pipette recordings were obtained from visually identified neurons using an infrared differential interference contrast (IR-DIC) video microscopy system. Intracellular patch solution for whole-cell IPSC current recordings contained (in mM) 120 Cs-gluconate, 10 HEPES, 11 EGTA, 11 $CsCl_2$, 1 $MgCl_2$, 1.25 QX314, 2 $Na_2$-ATP, 0.5 $Na_2$-GTP, (pH 7.25; 285-290 mOsm). To isolate GABAergic synaptic currents, slices were perfused with nACSF containing 20 µM 6,7-dinitroquinoxaline-2,3-dione (DNQX) and 50 µM d-(−)-2-amino-5-phosphonovaleric acid (D-APV). IPSCs were recorded at the reversal potential for glutamatergic currents (holding potential, 0 mV; room temperature) where IPSC events exhibit a large amplitude and prominent decay (Otis and Mody 1992). Intracellular patch pipette solution for current-clamp recordings contained (in mm) 120 KMeGluconate, 10 KCl, 1 $MgCl_2$, 0.025 $CaCl_2$), 10 HEPES, 0.2 EGTA, 2 Mg-ATP, 0.2 Na-GTP, pH 7.2, (285-290 mOsm). For analysis of intrinsic firing properties, recordings were obtained from GFP+ cells in the neocortex an IR-DIC microscope equipped with epifluorescence (Olympus). Current and voltage were recorded with an Axopatch 1D amplifier (Axon Instruments) and monitored on an oscilloscope. Cells were depolarized and hyperpolarized, via direct current injection (5-1000 ms, duration). Whole-cell access resistance was carefully monitored throughout the recording and cells were rejected if values changed by more than 25% (or exceeded 20 S2); only recordings with stable series resistance of <20 MΩ will be used for IPSC analysis (at least 100 events were analyzed per cell).

Video-EEG monitoring. Behavioral and electroencephalographic (EEG) observations were made using a time-locked, dual video digital EEG monitoring system (Pinnacle Technologies, Lawrence, Kans.). For EEG recordings, mice were surgically implanted in the left and right frontoparietal cortex with electrodes. Each mouse was anesthetized with ketamine and xylazine (10 mg/kg and 1 mg/kg, i.p. respectively) so that there was no limb withdrawal response to a noxious foot pinch. Sterile stainless steel recording electrodes were placed epidurally through burr holes in the skull (one electrode on either side of the sagittal suture, approximately halfway between bregman and lambdoid sutures and ~1 mm from the midline). Electrodes were cemented in place with a fast-acting adhesive and dental acrylic, and electrode leads were attached to a microplug that is also cemented to the head of the animal. Animals were allowed to recover for 5 days before experiments are initiated. Experimental animals were monitored for between 5-10 days (6-12 hr/day, 5 days/week; at least 30 hr per animal). A total of 165 hours of recording was analyzed for Kv1.1-1-mice (n=4) and 242 hours for Kv1.1-1-+ MGE mice (n=7). Control mice (n=4) were administered pilocarpine (300 mg/kg, i.p.) at the conclusion of the last recording session to obtain a "baseline" electrographic seizure sample. All monitoring data was coded and scored "blind" for changes in behavior and EEG by four independent investigators. Electrographic seizures were defined as follows (modified from Dube 2006; Wong 2007; Henshall 2002): Grade I, basic background, no epileptiform spikes; Grade II, mostly normal background, some high voltage spikes; Grade III, mostly abnormal background with low frequency high voltage spiking and Grade IV, high frequency, high voltage synchronized poly-spike or paroxysmal sharp-waves with amplitude >2-fold background that last 6 seconds. Electrographic EEG seizures were analyzed using SireniaScore software (Pinnacle) and confirmed by off-line review of behavioral video recordings obtained at two different monitoring angles. Behavior was scored, between Stage 1 (S1) and S4, on a modified Racine scale (Racine; Jones). All animals were sacrificed at the conclusion of EEG monitoring and processed for GFP immunohistochemistry and cell counting.

In some embodiments, patients with temporal lobe epilepsy, the most common form of the disease, are likely candidates for MGE therapy as it is well documented that interneuron loss contributes to the diseased state (de Lanerolle et al. 1989). In some embodiments, patients with epilepsy associated with a focal cortical dysplasia are also known to lose interneuron and/or exhibit reduced GABA-mediated inhibition (Spreafico et al. 1998; Calcagnotto et all 2005) and are also good candidates for MGE therapy. In some embodiments, clinical neuron-imaging studies (PET, MRI, etc.) in combination with video-EEG monitoring are used to identify candidate patients. In some embodiments, video-EEG monitoring and/or seizure self-reporting by patients is used to measure outcome of the MGE transplantation procedure. In some embodiments, MGE progenitor therapy success is quantified by a reduction in seizure frequency or duration in treated patients. In some embodiments, MGE progenitor therapy success is quantified by a reduction in dosages or the need for co-treatment with prescribed antiepileptic medications.

Note for figure legend: Kv1.1 is not the dominant Shaker family transcript expressed in vascular tissue (Cox et al. 2001). Kv1.1-containing potassium channels are predominantly expressed in axons of the hippocampus and cerebellum (Wang et al. 1993; Rhodes et al. 1997)

TABLE 1

Analysis of EEG data

| Animal | Duration (sec) | Frequency (per hr) | Highest seizure score |
|---|---|---|---|
| Kv1.1 KO | | | |
| #307 | 38.6 ± 3.7 | 0.6 ± 0.2 | Grade IV |
| #419 | 57.5*16.4 | 0.8 ± 0.3 | Grade IV |
| #461 | 59.0 ± 9.3 | 2.5 ± 0.1 | Grade IV |
| #466 | 58.0 ± 7.4 | 2.1 ± 0.6 | Grade IV |
| Kv1.1 KO + MGE | | | |
| #428 | 24.7 ± 2.2 | 0.1 ± 0.05 | Grade IV |
| #492 | 0 | 0 | Grade II |
| #525 | 0 | 0 | Grade II |
| #533 | 0 | 0 | Grade II |
| #544 | 23.7 ± 4.2 | 0.2 ± 0.15 | Grade IV |
| #573 | 27.5 ± 4.4 | 0.2 ± 0.07 | Grade IV |
| #575 | 28.0 ± 2.1 | 0.1 ± 0.08 | Grade IV |

Spasticity

Spasticity is a common disorder in patients with injury of the brain and spinal cord. The prevalence is approximately 65-78% of patients with spinal cord injury (Maynard et al. 1990), and around 35% in stroke patients with persistent hemiplegia (Sommerfeld et al. 2004). Reflex hyperexcitability develops over several months following human spinal cord injuries in segments caudal to the lesion site. Intractable spasticity is also a common source of disability in patients with multiple sclerosis. Symptoms include hypertonia, clonus, spasms and hyperreflexia.

There are numerous medicines that treat the general effects of spasticity. These drugs act on multiple muscle groups in the body. Tizanidine (Zanaflex Capsules™), temporarily reduces spasticity by blocking nerve impulses. Baclofen acts on the central nervous system to relax muscles. It also decreases the rate of muscle spasms, pain, tightness and improves range of motion. Benzodiazepines (Valium® and Klonopin®) act on the central nervous system to relax muscles and temporarily decrease spasticity. Dantrolene sodium (Dantrium®) acts directly on the muscle by blocking the signals that cause muscles to contract. Dantrolene use can lessen muscle tone. Injections of botulinum toxin (Botox® or Myobloc®) relax stiff muscles, but the shots only target specific limbs or muscle groups affected by spasticity. In more extreme cases, intrathecal baclofen or surgery is used to relieve spasticity.

While the precise mechanisms responsible for the development of spasticity are not fully understood, a role for reduction of inhibition is most likely involved. For example, inhibitory interneurons are particularly vulnerable to spinal cord ischemic injury, and are often selectively lost following spinal cord injury. This may contribute to the changes in inhibitory circuits observed following spinal injury such as reduction in reciprocal inhibition as well as attenuation of inhibition normally mediated by segmental inhibitory interneurons that synapse directly onto motoneurons.

The treatment of spasticity is treated by grafting inhibitory interneurons (MGE cells) into the affected segments of the injured spinal cord. The GABAergic cells derived from the median ganglionic eminence (MGE) will down-regulate the hyperactive local spinal circuitry. In the developing brain, MGE cells gives rise to inhibitory neurons, and this particular class of neuron has a remarkable ability to migrate and integrate in adult brain tissue. MGE cells will integrate in the spinal cord and produce factors that will inhibit local circuit activity and reduce post-lesion spasticity. This strategy can also be used to relieve spasticity in a variety of other conditions including multiple sclerosis, stroke, and brain injury.

Example 5 (Prophetic)

Generation of a Spinal Cord Injury in Mice

Genetically modified and wild-type mice are anesthetized with Avertin supplemented with isoflurane or isoflurane only. The skin over the middle of the back is shaved. The shaved area is disinfected with Clinidine. All surgical tools are soaked overnight in Cidex prior to their use. Lubricating ophthalmic ointment is placed in each eye. Animals are placed on a warming blanket to maintain temperature at 37° C. A dorsal midline incision, approximately 1 cm in length is made using a scalpel blade. The spinous process and lamina of T9 are identified and removed. A circular region of dura, approximately 2.4 mm in diameter, is exposed. At this point the animal is transferred to the spinal cord injury device that is about 5 feet from the surgical area. Small surgical clamps are placed on a spine rostral and a spine caudal to laminectomy site to stabilize the vertebral column. Thereafter, a 2-3 g weight is dropped 5.0 cm onto the exposed dura. This produces a moderate level of spinal cord injury. Immediately after injury, the animal is removed from the injury device and returned to the surgical area. A small, sterile suture is placed in the paravertebral musculature to mark the site of injury. The skin is then closed with wound clips and the animal recovered from the anesthesia. The entire surgical procedure is completed within 45 to 60 minute.

Assessment of Motor Function in Mice

Spinal cord injured mice are euthanized at 1 hour to 42 days after injury. In those animals that survive 42 days, locomotor ability is evaluated as follows:

Open field testing. This involves testing animals at 3 days and weekly thereafter until time of euthanasia at 42 days. Locomotor testing consists of evaluating how animals locomote in an open field. This open field walking score measures recovery of hindlimb movements in animals during free open field locomotion as described by Basso et al. A score of 0 is given if there is no spontaneous movement, a score of 21 indicate normal locomotion. Plantar stepping with full weight support and complete forelimb-hindlimb coordination is reached when an animal shows a score of 14 points. We use a modified version of the BBB score if the sequence of recovering motor features is not the same as described in the original score. If this is observed, points for the single features are added independently. For example, a mouse showing incomplete toe clearance, enhanced foot rotation and already a 'tail-up' position, one additional point are added to the score for the tail position.

The mice are tested preoperatively in an open field, which was an 80×130-cm transparent plexiglass box, with walls of 30 cm and a pasteboard covered non-slippery floor. In postoperative sessions two people, blinded to the treatments, will observe each animal for a period of 4 min. Animals that exhibit coordinated movement, based upon open field testing, are subjected to additional tests of motor function as follows.

Grid walking. Deficits in descending motor control are examined by assessing the ability of the animals to navigate across a 1 m long runway with irregularly assigned gaps (0.5-5 cm) between round metal bars. The bar distances are randomly changed from one testing session to the next. The animals are tested over a period of 5 days, beginning 1 to 2 weeks prior to euthanasia.

Crossing this runway requires that animals accurately place their limbs on the bars. In baseline training and postoperative testing, every animal will cross the grid for at least three times. The number of footfalls (errors) are counted in each crossing and a mean error rate is calculated. If an animal is not able to move the hindlimbs, a maximum of 20 errors are given. The numbers of errors counted are also rated in a non-parametric grid walk score: 0-1 error is rated as 3 points, 2-5 as 2 points, 6-9 as 1 point and 10-20 footfalls as 0 points.

Foot placement. Footprint placement analysis is modified from De Medinaceli et al. The animal's hind paws are inked, for example, with watercolor paint that can easily be washed off, and footprints are made on paper covering a narrow runway of 1 m length and 7 cm width as the animals traverse the runway. This ensures that the direction of each step is standardized in line. A series of at least eight sequential steps are used to determine the mean values for each measurement of limb rotation, stride length and base of support. The base of support are determined by measuring the core to core distance of the central pads of the hind paws. The limb rotation are defined by the angle formed by the intersection of the line through the print of the third digit and the print representing the metatarsophalangeal joint and the line through the central pad parallel to the walking direction. Stride length are measured between the central pads of two consecutive prints on each side.

To include animals with incomplete weight support in early postoperative testing sessions, a 4-point scoring system is also used: 0 points is given for constant dorsal stepping or hindlimb dragging, i.e. no footprint was visible; 1 point is counted if the animal had visible toe prints of at least three toes in at least three footprints; 2 points are given if the animal showed exo- or endo-rotation of the feet of more than double values as compared to its own baseline values; 3 points are recorded if the animal showed no signs of toe dragging but foot rotation; 4 points are rated if the animal showed no signs of exo- or endo-rotation (less than twice the angle of the baseline values). These animals are tested over a period of 5 days, beginning 1 to 2 weeks prior to euthanasia.

Beam balance. Animals are placed on a narrow beam, and the ability to maintain balance and/or traverse the beam is evaluated. These animals are tested over a period of 5 days, beginning 1 to 2 weeks prior to euthanasia. The narrow beat test is performed according to the descriptions of Hicks and D'Amato. Three types of beams are used as narrow pathways: a rectangular 2.3 cm wide bean, a rectangular 1.2 cm wide beam and a round dowel with 2.5 cm diameter. All beams are 1 m long and elevated 30 cm from the ground.

After training, normal rats are expected to be able to traverse the horizontal beams with less than three footfalls. When occasionally their feet slipped off the beam, the animals are retrieved and repositioned precisely.

A scoring system is used to assess the ability of the animals to traverse the beams: 0 is counted as complete inability to walk on the bean (the animals fall down immediately), 0.5 is scored if the animal was able to traverse half of the beam, 1 point is given for traversing the whole length, 1.5 points when stepping with the hindlimbs is partially possible, and 2 points is noted for normal weight support and accurate foot placement. If the scores of all three beams are added, a maximum of 6 points can be reached.

Inclined plane. Animals are placed on a platform that can be raised to varying angles. The ability to maintain position at a given angle is determined. These animals are tested over a period of 5 days, beginning 1 to 2 weeks prior to euthanasia. Animals are placed on an adjustable inclined plane constructed as described (Rivlin and Tator, 1977). The slope is progressively increased every 20 s noting the angle at which the mouse could not maintain its position for 5 s. The test is repeated twice for each mouse and the average angle is recorded. In the inclined-plane test, recovery from motor disturbance is assessed before, and again at 1, 7, 14, and 21 d after the injury. The maximum inclination of the plane on which the rats could maintain themselves for 5 sec without falling is recorded.

Each of these tests described above takes less than 5 minutes. These various tests are designed such that if animals fall from the testing apparatus, they either land on padded flooring or the distance fallen is sufficiently limited (less than 6 inches) that the animals are not be harmed.

Generation of a Spinal Cord Injury in Rats

MGE cells are implanted into the uninjured cord of rats to assess their integration into the local circuitry (n=10) and also into contused (n=10) and transected (n=10) spinal cords. Both contusion and transection are studied in order to assess mild (contusion) and moderate (transection) levels of spasticity.

Rats are anesthetized with Avertin supplemented with isoflurane or isoflurane only. The skin over the middle of the back is shaved. The shaved area is disinfected with Clinidine. All surgical tools are soaked overnight in Cidex prior to their use. Lubricating ophthalmic ointment is placed in each eye. Animals are placed on a warming blanket to maintain temperature at 37° C. A dorsal midline incision, approximately 1 cm in length is made using a scalpel blade. The spinous process and lamina of T9 are identified and removed. A circular region of dura, approximately 2.4 mm in diameter, is exposed.

To produce a contusion injury, a circular region of dura, approximately 3.0 mm in diameter, is exposed. At this point the animal is transferred to the spinal cord injury device that is about 5 feet from the surgical area. Small surgical clamps are placed on a spine rostral and a spine caudal to laminectomy site to stabilize the vertebral column. Thereafter, a 10 g weight is dropped 5 cm onto the exposed dura. This produces a moderate level of spinal cord injury. To produce a transection injury, the procedure to expose the cord is similar to that for the contusion injury except a surgical blade is used to completely transect the spinal cord.

Immediately after contusion or transection injury, the animal is removed from the injury device and returned to the surgical area. A small, sterile suture is placed in the paravertebral musculature to mark the site of injury. The skin is then closed with wound clips and the animal recovered from the anesthesia. The entire surgical procedure is completed within 45 to 60 minutes.

Spinal Cord Implantation of MGE Cells in Rats

The first surgery produces either a contusion or transection spinal cord injury as described. Spasticity is initially seen at seven days after injury. A second surgery on day 7 is used to inject MGE cells into the injured spinal cord. The delay in MGE implantation allows the ability to measure reductions in spasticity over time.

Seven days after either transection or contusion, animal are re-anesthetized with isoflurane, the exposed cord is visualized and two additional laminectomies are made caudal to the original laminectomy. Using a stereotaxic device, MGE cells, are injected into each of the ventral horns. An uninjured control group is also be injected with cells. A sterile suture is positioned in the paravertebral musculature to mark the surgical site. The skin is then closed with wound clips and the animal is recovered from the anesthesia. This transplantation procedure is completed in approximately 60 minutes. Spinal cord injured and control rats are anesthetized and perfused with fixative at 1 to 6 weeks after transplantation of cells.

Assessment of Motor Function in Rats

After recovery from surgery, these animals may be assessed for function 1-2 times weekly:

Locomotor assessment. Locomotor testing consists of evaluating how animals locomote in an open field. One day postinjury (p.i.) and 1 to 2 times weekly thereafter, behavioral analysis is performed by two observers blinded to the treatments, using a battery of tests to rate open-field locomotion by the Basso-Beattie-Bresnahan (BBB) scale. This open field walking score measures recovery of hindlimb movements in rats during free open field locomotion as described by Basso et al. A score of 0 is given if there is no spontaneous movement, a score of 21 indicate normal locomotion. Plantar stepping with full weight support and complete forelimb-hindlimb coordination is reached when an animal shows a score of 14 points. We will use a modified version of the BBB score if the sequence of recovering motor features is not the same as described in the original score. If this is observed, points for the single features are added independently. For example, a rat showing incomplete toe clearance, enhanced foot rotation and already a 'tail-up' position, one additional point are added to the score for the tail position.

The rats are tested preoperatively in an open field, which was an 80×130-cm transparent plexiglass box, with walls of 30 cm and a pasteboard covered non-slippery floor. In postoperative sessions two people, blinded to the treatments, will observe each animal for a period of 4 min. Animals that exhibit coordinated movement, based upon open field testing, are subjected to additional tests of motor function as follows.

Grid walking. Deficits in descending motor control are examined by assessing the ability of the animals to navigate across a 1 m long runway with irregularly assigned gaps (0.5-5 cm) between round metal bars. The bar distances are randomly changed from one testing session to the next. The animals are tested 1 to 2 times weekly postinjury. Crossing this runway requires that animals accurately place their limbs on the bars. In baseline training and postoperative testing, every animal will cross the grid for at least three times. The number of footfalls (errors) are counted in each crossing and a mean error rate is calculated. If an animal is not able to move the hindlimbs, a maximum of 20 errors are given. The numbers of errors counted are also rated in a non-parametric grid walk score: 0-1 error is rated as 3 points, 2-5 as 2 points, 6-9 as 1 point and 10-20 footfalls as 0 points.

Foot placement. Footprint placement analysis is modified from De Medinaceli et al. The animal's hind paws are inked, for example, with watercolor paint that can easily be washed off, and footprints are made on paper covering a narrow runway of 1 m length and 7 cm width as the animals traverse the runway. This ensures that the direction of each step is standardized in line. A series of at least eight sequential steps are used to determine the mean values for each measurement of limb rotation, stride length and base of support. The base of support are determined by measuring the core to core distance of the central pads of the hind paws. The limb rotation are defined by the angle formed by the intersection of the line through the print of the third digit and the print representing the metatarsophalangeal joint and the line through the central pad parallel to the walking direction. Stride length are measured between the central pads of two consecutive prints on each side.

To include animals with incomplete weight support in early postoperative testing sessions, a 4-point scoring system is also used: 0 points is given for constant dorsal stepping or hindlimb dragging, i.e. no footprint was visible; 1 point is counted if the animal had visible toe prints of at least three toes in at least three footprints; 2 points are given if the animal showed exo- or endo-rotation of the feet of more than double values as compared to its own baseline values; 3 points are recorded if the animal showed no signs of toe dragging but foot rotation; 4 points are rated if the animal showed no signs of exo- or endo-rotation (less than twice the angle of the baseline values).

Beam balance. Animals are placed on a narrow beam, and the ability to maintain balance and/or traverse the beam is evaluated. The narrow beat test is performed according to the descriptions of Hicks and D'Amato. Three types of beams are used as narrow pathways: a rectangular 2.3 cm wide bean, a rectangular 1.2 cm wide beam and Three types of beams are used as narrow pathways: a rectangular 2.3 cm wide bean, a rectangular 1.2 cm wide beam and a round dowel with 2.5 cm diameter. All beams are 1 m long and elevated 30 cm from the ground. After training, normal rats are expected to be able to traverse the horizontal beams with less than three footfalls. When occasionally their feet slipped off the beam, the animals are retrieved and repositioned precisely.

A scoring system is used to assess the ability of the animals to traverse the beams: 0 is counted as complete inability to walk on the bean (the animals fell down immediately), 0.5 is scored if the animal was able to traverse half of the beam, 1 point is given for traversing the whole length, 1.5 points when stepping with the hindlimbs is partially possible, and 2 points is noted for normal weight support and accurate foot placement. If the scores of all three beams are added, a maximum of 6 points can be reached.

Inclined plane. Animals are placed on a platform that can be raised to varying angles. The ability to maintain position at a given angle is determined.

Animals are placed on an adjustable inclined plane constructed as described (Rivlin and Tator, 1977). The slope is progressively increased every 20 s noting the angle at which the mouse could not maintain its position for 5 s. The test is repeated twice for each mouse and the average angle is recorded. In the inclined-plane test, recovery from motor disturbance is assessed before, and again at 1, 7, 14, and 21 d after the injury. The maximum inclination of the plane on which the rats could maintain themselves for 5 sec without falling is recorded.

Each of these tests described above takes less than 5 minutes. These various tests are designed such that if animals fall from the testing apparatus, they either land on padded flooring or the distance fallen is sufficiently limited (less than 6 inches) that the animals are not harmed.

Transplantation of MGE progenitor cells can be used in methods of the present disclosure reduce spasticity (e.g., as seen in multiple sclerosis, stroke, and brain injury) by at least 10% compared to controls, or the individual's previously untreated stated. In some embodiments, transplantation of MGE progenitor cells reduces spasticity by at least 20%, 30%, 40%, 50%, 60%, 70%, 80%, 90%, or 95% compared to controls, or the individual's previously untreated stated. In some embodiments, transplantation of MGE progenitor cells reduces the need for medication by at least 10% compared to controls, or the individual's previously untreated stated. In some embodiments, transplantation of MGE progenitor cells reduces the need for medication by at least 20%, 30%, 40%, 50%, 60%, 70%, 80%, 90%, or 95% compared to controls, or the individual's previously untreated stated. In some embodiments, transplantation of MGE progenitor cells obviates the need for intrathecal medication or surgery.

In Vitro Expansion of MGE Progenitor Cells (Prophetic Example)

The practical and ethical problems associated with embryonic and fetal tissue transplantation is overcome through the use of in vitro expansion of a small amount of embryonic or fetal CNS tissue as floating cell aggregates called neurospheres using the technique developed by Reynolds, B. A., and Weiss, S., Generation of neurons and astrocytes from isolated cells of adult mammalian central nervous system. Science 255: 1707-1710, 1992.

Primary Cultures and Passaging Procedures

Adult pregnant rats are anesthetized with ketamine (90 mg/Kg) and xylazine (7 mg/Kg). Fetuses are removed from the uterus at E14.5 and brains dissected under a microscope. The MGE is dissected from the forebrain in oxygenated artificial cerebrospinal fluid (aCSF, in mm: NaCl, 125; KCl, 2.5; MgCl2, 1; CaCl2, 2; NaPO4, 1.25; NaHCO3, 25; and glucose, 25; Sigma). Twelve to 15 MGEs are dissected and prepared as described in Reynolds and Weiss. The culture medium is DMEM/F12 supplemented with the hormone mixture used by Reynolds and Weiss along with human recombinant fibroblast growth factor-2 (FGF-2; 20 ng/ml; Prepro Tech, Inc., Rocky Hill, N.J.). Fresh FGF-2 is added every 2 days. Cells are passages once per week. The passage of cells obtained from one pregnant rat (12-15 fetuses) three times will produce enough immature neural progenitor cells for the transplantation of at least 450 rats. Thus, the in vitro expansion of embryonic or fetus-derived MGE progenitor cells using the above methodology or other methodology known to one of skill in the art is a useful source for transplantable material with which to treat neurological conditions, disease, or injury, including Parkinson's disease, epilepsy, and spinal cord injury.

Generation of an Immortalized Cell Line that is Substantially Similar to MGE Cells Isolated from E13.5 Mouse Fetus (Prophetic Example)

Normal human somatic cells have a defined life span and enter senescence after a limited number of cell divisions. At senescence, cells are viable but no longer divide. This limitation on cell proliferation represents an obstacle in the scale up and production of large quantities of MGE progenitor cells required for transplantation. The establishment of permanent cell lines will circumvent this problem. Many immortalized tumor cell lines are known and normal human somatic cells can be transformed in vitro with oncogenes to establish permanent cell lines. While valuable for research, transformed cells derived from normal human cells are unacceptable for therapeutic use owing to their alterations in cell cycle, loss of contact inhibition, aneuploidy, spontaneous hypermutability and other characteristics associated with cancerous cells.

Fortunately, the recognition that replicative senescence is controlled by the shortening of the telomeres allows for the production of immortalized cell lines through methodologies that modulate or control the regulation of telomerase. One of the number of ways known in the art to immortalize cells is by the forced expression of exogenous hTERT in normal human cells. This produces telomerase activity and prevent the erosion of telomeres and resultant senescence. MGE progenitor cells immortalized with hTERT have normal cell cycle controls, functional p53 and pRB checkpoints, are contact inhibited, are anchorage dependent, require growth factors for proliferation and possess a normal karyotype. Thus MGE progenitor cells that express exogenous hTERT have extended life spans that allow for the production of useful quantities of MGE progenitor cells for transplantation.

Methods and Materials

Telomerase is introduced into MGE progenitors using the techniques of Ouellette, M. M. et al. The establishment of telomerase-immortalized cell lines representing human chromosome instability syndromes. Human Molecular Genetics, 9:403-411, 2000. Briefly, retroviral supernatants is obtained from PA317 packaging cells stably expressing hTERT cloned into the pBabepuro vector. Cells are infected and then selected for 2 weeks using puromycin at 750 ng/ml.

Cells are grown at 37° C. in 5% $CO_2$ Neurobasal™ Medium (Invitrogen, Purchase, N.Y.) and Gentamicin (25 μg/ml). For hygromycin B sensitivity, cells were grown at various doses for 7 days, stained for viability and counted.

Telomerase activity is determined using the TRAP assay (TRAPeze kit, Intergen, Purchase, N.Y.). PCR products are electrophoresed on 10% polyacrylamide gels and quantified using the Phosphorimaging system and IMAGEQUANT (Molecular Dynamics, Amersham Pharmacia Biotech, Piscataway, N.J.). Quantitation of telomerase activity is done by determining the ratio of the 36 bp internal standard to the telomerase ladder.

Total genomic DNA is isolated as described in Ouellette, M. M., et al. Telomerase activity does not always imply telomere maintenance. Biochem. Biophys. Res. Commun., 254:795-803,1999. The DNA is digested with a battery of six enzymes (HinfI, RsaI, CfoI, AluI, HaeIII, MspI) and resolved on a 1% agarose gel. The gel is denatured and dried, neutralized and the signal detected in situ using a telomeric probe end-labeled with $[\gamma-^{32}P]ATP$.

The immortalized MGE progenitor cell line is compared with uninfected MGE progenitor cells to demonstrate: (i) the presence of telomerase activity; (ii) the capacity to maintain extended telomere size; and (iii) the ability to grow beyond the number of population doublings of uninfected control MGE progenitor cells. Using the telomere repeat amplification protocol (TRAP) assay, telomerase activity should be found to be absent from all uninfected samples, but present in samples that are infected with the hTERT vector. Preferably, the level of activity detected in the infected cells should be comparable with that detected in a human lung cancer cell line, H1299, with telomere size larger in the immortalized MGE progenitor cells than in their uninfected counterpart, indicating the exogenous telomerase activity is able to elongate telomeres. All samples are continuously passaged to determine cellular life span. Uninfected samples would be expected to enter senescence after approximately 60 population doublings, and thus the presence of exogenous telomerase preferably should extend the life span of MGE progenitor cells by at least three-fold compared to the uninfected cultures.

REFERENCES

The following references are cited in the specification: Alvarez-Dolado M, et al., 2006, J Neurosci 26(28):7380-7389; Anderson S, et al., 1997, Neuron 19(1):27-37; Anderson S, et al., 1999, Cereb Cortex 9(6):646-654; Benabid A L, et al., 2000, Archives of medical research 31(3):282-289; Berger K, et al., 1991, Brain research bulletin 26(2):301-307; Bhattacharya N, et al., 2004, Trends biomater Artif Organs 17(2):78-89; Butt S J, et al., 2005, Neuron 48(4):591-604; Calcagnotto, M. E. et al., 2005, J Neurosci 25, 9649-57; Campbell K et al., 1995, Neuron 15(6):1259-1273; Chu, K. et al., 2004, Brain Res 1023, 213-21; Creese I et al., 1977, Science (New York, N.Y. 197(4303):596-598; de Lanerolle, N. O et al., Brain Res 495, 387-95(1989); Deacon T W et al., 1994, Brain Res 668(1-2):211-219; Defelipe J et al., 1999, The Journal of comparative neurology 412(3):515-526; DeLong M R and Wichmann T, 2007, Archives of neurology 64(1):20-24; Dichter, M. and Spencer W. A, 1969, J Neurophysiol 32, 649-662; Dube, C. et al. Brain 129, 911-22 (2006); During M J, et al., 2001, Human gene therapy 12(12):1589-1591; Glasscock, E., et al., Nat Neurosci 10, 1554-8 (2007); Grasbon-Frodl E, et al., 1997, Neurobiol Dis 3(4):299-311; Haberman, R. P., et al., Nat Med 9, 1076-80 (2003); Hamani, C. Et al., Epilepsy Res 49, 73-80 (2002); Henshall, D. C. et al. Neurobiol Dis 10, 71-87 (2002); Huber, A. et al. Proc Natl Acad Sci USA 98, 7611-6 (2001); Hudson J L et al., 1993, Brain research 626(1-2):167-174; Jones, D. M. et al., Epilepsy Res 50, 301-12 (2002); Kanter-Schlifke, I. Et al. Mol Ther 15, 1106-13 (2007); Kawaguchi Y, et al. 1995, Trends in neurosciences 18(12):527-535; Koos T et al., 2004, J Neurosci 24(36):7916-7922; Koos T and Tepper J M. 1999 Nature Neuroscience 2(5):467-472; Kubota Y, et al., 1994, Brain Res 649(1-2):159-173; Larsson E, et al., 2001, Brain Res 913 (2):117-132; Lavdas A A, et al., 1999, J Neurosci 19(18):7881-7888; Lee B, et al. 2005 Gene therapy 12(15):1215-1222; Li Q J, et al. 2007 Synapse NY 61(12):971-977; Li, T. et al. Brain 130, 1276-88 (2007); Litvan I, et al., 2007, J. Neuropathol. Experim. Neurol. 66(4):251-257; Luk K C and Sadikot A F. 2001 Neuroscience 104(1):93-103; Marin O et al., 2000, J Neurosci 20(16):6063-6076; McCown, T. J. Mol Ther 14, 63-8 (2006); Mody, I. J Physiol 562, 37-46 (2005); Noctor S C, et al. 2008, The Journal of comparative neurology 508(1):28-44; Noebels, J. L. Annu Rev Neurosci 26, 599-625 (2003); Olson L et al. 1991 Archives of neurology 48(4):373-381; Olsson M, et al., 1997 Neuroscience 79(1):57-78; Olsson M, et al., 1998, Neuroscience 84(3):867-876; Olsson M, et al., 1995, Neuroscience 69(4):1169-1182; Otis, T. S. & Mody, I. Neuroscience 49, 13-32 (1992); Paxinos et al. 1982. The Rat Brain in Stereotaxic Coordinates. New York: Academic Press; Plenz D, Kitai S T. 1998. J Neurosci 18(1):266-283; Pow D V, et al., 2005, Cell and tissue research 320(3):379-392; Racine, R. J. Electroencephalogr Clin Neurophysiol 32, 281-94 (1972); Richichi, C. et al. J Neurosci 24, 3051-9 (2004); Rymar V V, et al., 2004, Journal of comparative neurology 469(3):325-339; Shetty, A. K., et al. J Neurosci 25, 8391-401 (2005); Smart, S. L et al. Neuron 20, 809-19 (1998); Sofia, R. D, et al., Res Commun Chem Pathol Pharmacol 79, 335-41 (1993); Spreafico, R. et al. Neurology 50, 27-36 (1998); Tepper J M, Bolam J P. 2004, Current opinion in neurobiology 14(6):685-692; Thompson, K. et al. Exp Neurol 161, 481-9 (2000); Thompson, K. W. Neuroscience 133, 1029-37 (2005); Ungerstedt U, Arbuthnott G W. 1970 Brain Res 24(3):485-493; Wenzel, H. J. et al. Epilepsia 48, 2023-46 (2007); West M J, et al., 1996 The Journal of comparative neurology 370(1):11-22; Winawer, M. R. et al. Neuroscience 149, 465-75 (2007); Xu, Y. et al. Biochem Biophys Res Commun 361, 499-504 (2007); Zigmond M J, et al., 1984 Archives of neurology 41(8):856-861; Zuberi, S. M. et al. Brain 122 (Pt 5), 817-25 (1999).

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for the treatment of a mammal with a chronic pain disorder associated with a neurological condition, comprising:
   depositing medial ganglionic eminence (MGE) precursor cells at desired delivery sites in the nervous system of the mammal, and
   wherein the MGE precursor cells are genetically modified to express an exogenous protein.

2. The method of claim 1, wherein the exogenous protein allows tracking of the MGE precursor cells following transplantation or wherein the exogenous protein is a neurotransmitter producing enzyme, a neurotrophin, a neural promoting growth factor, a neural inhibitory growth factor, or a neuropoietic cytokine.

3. The method of claim 1, wherein the exogenous protein is a telomerase.

4. The method of claim 1, further comprising assessing an improvement of the symptoms of the chronic pain disorder in the treated mammal.

5. The method of claim 1, wherein the neurological condition comprises nerve injury.

6. The method of claim 1, wherein the chronic pain is neuropathic pain resulting from a spinal cord injury.

7. The method of claim 1, wherein the MGE precursor cells are deposited by injection.

8. The method of claim 1, wherein the MGE precursor cells are deposited into the peripheral nervous system.

9. The method of claim 1, wherein the mammal does not require immunosuppressive therapy following treatment.

10. The method of claim 1, wherein the MGE precursor cells are deposited into the brain or spinal cord.

11. A method for the treatment of a mammal with a chronic pain disorder associated with a neurological condition, comprising:
    depositing medial ganglionic eminence (MGE) precursor cells at desired delivery sites in the nervous system of the mammal, and
    wherein the MGE precursor cells are genetically modified to modulate expression of a protein associated with neural function, wherein the protein is a neurotransmitter producing enzyme, a neurotrophin, a neural promoting growth factor, a neural inhibitory growth factor, a neuropoietic cytokine, or a telomerase.

12. The method of claim 11, wherein the protein is a telomerase.

13. The method of claim 11, wherein the protein is a neurotransmitter producing enzyme, a neurotrophin, a neural promoting growth factor, a neural inhibitory growth factor, or a neuropoietic cytokine.

14. The method of claim 11, further comprising assessing an improvement of the symptoms of the chronic pain disorder in the treated mammal.

15. The method of claim 11, wherein the neurological condition comprises nerve injury.

16. The method of claim 11, wherein the chronic pain is neuropathic pain resulting from a spinal cord injury.

17. The method of claim 11, wherein the MGE precursor cells are deposited by injection.

18. The method of claim 11, wherein the MGE precursor cells are deposited into the peripheral nervous system.

19. The method of claim 11, wherein the mammal does not require immunosuppressive therapy following treatment.

20. The method of claim 11, wherein the MGE precursor cells are deposited into the brain or spinal cord.

\* \* \* \* \*